United States Patent
Krams et al.

(10) Patent No.: US 9,623,040 B2
(45) Date of Patent: Apr. 18, 2017

(54) IMMUNOMODULATION BY CONTROLLING EXPRESSION LEVELS OF MICRORNAS IN DENDRITIC CELLS

(71) Applicants: The Board of Trustees of the Leland Stanford Junior University, Palo Alto, CA (US); The Regents of the University of California, Oakland, CA (US)

(72) Inventors: Sheri M. Krams, Berkeley, CA (US); Audrey H. Lau, Menlo Park, CA (US)

(73) Assignees: The Board of Trustees of the Leland Stanford Junior University, Stanford, CA (US); The Regents of the University of California, Oakland, CA (US)

( * ) Notice: Subject to any disclaimer, the term of this patent is extended or adjusted under 35 U.S.C. 154(b) by 0 days.

(21) Appl. No.: 14/797,065

(22) Filed: Jul. 10, 2015

(65) Prior Publication Data

US 2016/0008397 A1 Jan. 14, 2016

Related U.S. Application Data

(60) Provisional application No. 62/024,332, filed on Jul. 14, 2014.

(51) Int. Cl.
| | |
|---|---|
| *C07H 21/02* | (2006.01) |
| *C07H 21/04* | (2006.01) |
| *A61K 48/00* | (2006.01) |
| *A61K 31/7105* | (2006.01) |
| *A61K 45/06* | (2006.01) |
| *C12N 15/113* | (2010.01) |
| *C12N 5/00* | (2006.01) |
| *A61K 35/12* | (2015.01) |
| *A61K 35/15* | (2015.01) |

(52) U.S. Cl.
CPC .......... *A61K 31/7105* (2013.01); *A61K 45/06* (2013.01); *A61K 48/00* (2013.01); *C12N 5/00* (2013.01); *C12N 15/113* (2013.01); *A61K 35/15* (2013.01); *A61K 2035/122* (2013.01); *C12N 2310/141* (2013.01)

(58) Field of Classification Search
CPC .......................... C12N 15/113; C12N 2310/11
See application file for complete search history.

(56) References Cited

U.S. PATENT DOCUMENTS

| 7,803,784 B2 | 9/2010 | Li et al. |
|---|---|---|
| 8,247,388 B2 | 8/2012 | Chen et al. |
| 2009/0010948 A1 | 1/2009 | Huang et al. |
| 2010/0266555 A1 | 10/2010 | Skjode Jensen et al. |
| 2011/0201008 A1 | 8/2011 | Lossos et al. |
| 2012/0041048 A1* | 2/2012 | Weinberg ............ C12N 15/113 514/44 A |

FOREIGN PATENT DOCUMENTS

| WO | 2007081740 A2 | 7/2007 |
|---|---|---|
| WO | 2007103808 A2 | 9/2007 |
| WO | 2012046065 A2 | 4/2012 |
| WO | 2013060894 A1 | 5/2013 |
| WO | 2014006160 A1 | 1/2014 |

OTHER PUBLICATIONS

Turner et al. (The Journal of Immunology, Oct. 15, 2011, vol. 187, No. 8, 3911-3917).*
Gupta et al. (2010) Elevated myeloid: plasmacytoid dendritic cell ratio associates with early acute cellular rejection in pediatric small bowel transplantation. Transplantation 89(1):55-60.
Wei et al.( 2012) Differential Expression of MicroRNAs During Allograft Rejection. AJT 12(5):1113-1123.
Wei et al. (2013) Differential expression and functions of microRNAs in liver transplantation and potential use as non-invasive biomarkers. Transpl. Immunol. 29(1-4):123-129.
Harris et al. (2010) MicroRNAs as immune regulators: implications for transplantation. Am. J. Transplant 10(4):713-719.
Shan et al. (2011) MicroRNAs: Potential biomarker in organ transplantation. Transpl. Immunol. 24(4):210-215.
Pedersen et al. (2008) MicroRNAs in the immune response. Cytokine 43:391-394.
Wu et al. (2012) MicroRNA-181a represses ox-LDL-stimulated inflammatory response in dendritic cell by targeting c—Fos. J. Lipid Res. 53(11):2355-2363.
Lwin et al. (2010) Follicular dendritic cell-dependent drug resistance of non-Hodgkin lymphoma involves cell adhesion-mediated Bim down-regulation through induction of microRNA-181a. Blood 116(24):5228-5236.
Luo et al. (2012) Functional Analysis of Alloreactive Memory CD4D T Cells Derived from Skin Transplantation Recipient and Na€ive CD4D T Cells Derived from Untreated Mice. J. Surg. Res. 176(2):649-656.
Li et al. (2009) Knockdown of microRNA-181 by lentivirus mediated siRNA expression vector decreases the arrhythmogenic effect of skeletal myoblast transplantation in rat with myocardial infarction. Microvasc Res. 78(3):393-404.
Hickey et al. (2013) Lenalidomide-mediated enhanced translation of C/EBP-p30 protein up-regulates expression of the antileukemic microRNA-181a in acute myeloid leukemia. Blood 121(1):159-169.

(Continued)

*Primary Examiner* — Amy Bowman
(74) *Attorney, Agent, or Firm* — Jenny Buchbinder

(57) ABSTRACT

Compositions and methods of modulating an immune response by controlling expression levels of microRNAs in dendritic cells are disclosed. In particular, the invention relates to modified dendritic cells and methods of using such dendritic cells in cellular therapy for treating various immune conditions and diseases, including transplant rejection, inflammatory disorders, autoimmune diseases, allergies, infectious diseases, immunodeficiency, and cancer.

25 Claims, 10 Drawing Sheets

(56) References Cited

OTHER PUBLICATIONS

Chen et al. (2013) Regulation of immune responses and tolerance: the microRNA perspective. Immunol. Rev. 253(1):112-128.
Henao-Mejia et al. (2013) The microRNA miR-181 is a critical cellular metabolic rheostat essential for NKT cell ontogenesis and lymphocyte development and homeostasis. Immunity 38(5):984-997.
Li et al. (2007). miR-181a is an intrinsic modulator of T cell sensitivity and selection. Cell 129 (1):147-161.
Turner et al. (2011) MicroRNAs Regulate Dendritic Cell Differentiation and Function. J. Immunol. 187:3911-3917.
Sui et al. (2008) Microarray analysis of MicroRNA expression in acute rejection after renal transplantation. Transpl. Immunol. 19:81-85.
Veit et al. (2009) Tolerance versus immune response—MicroRNAs as important elements in the regulation of the HLA-G gene expression. Transpl. Immunol. 20:229-231.
Dewi et al. (2013) Altered serum miRNA profiles during acute rejection after heart transplantation: potential for non-invasive allograft surveillance. J. Heart Lung Transplant 32(4):463-466.

\* cited by examiner

SEQUENCE LISTING

```
<160> NUMBER OF SEQ ID NOS: 6

<210> SEQ ID NO 1
<211> LENGTH: 110
<212> TYPE: DNA
<213> ORGANISM: Homo sapiens
<300> PUBLICATION INFORMATION:
<308> DATABASE ACCESSION NUMBER: NCBI/NR_029626
<309> DATABASE ENTRY DATE: 2014-04-06
<313> RELEVANT RESIDUES IN SEQ ID NO: (1)..(110)

<400> SEQUENCE: 1
```
tgagttttga ggttgcttca gtgaacattc aacgctgtcg gtgagtttgg aattaaaatc    60
aaaaccatcg accgttgatt gtaccctatg gctaaccatc atctactcca              110

<210> SEQ ID NO 2
<211> LENGTH: 110
<212> TYPE: DNA
<213> ORGANISM: Homo sapiens
<300> PUBLICATION INFORMATION:
<308> DATABASE ACCESSION NUMBER: NCBI/NR_029611
<309> DATABASE ENTRY DATE: 2014-02-27
<313> RELEVANT RESIDUES IN SEQ ID NO: (1)..(110)

<400> SEQUENCE: 2
agaagggcta tcaggccagc cttcagagga ctccaaggaa cattcaacgc tgtcggtgag    60
tttgggattt gaaaaaacca ctgaccgttg actgtacctt ggggtcctta              110

<210> SEQ ID NO 3
<211> LENGTH: 110
<212> TYPE: DNA
<213> ORGANISM: Homo sapiens
<300> PUBLICATION INFORMATION:
<308> DATABASE ACCESSION NUMBER: NCBI/NR_029612
<309> DATABASE ENTRY DATE: 2014-05-11
<313> RELEVANT RESIDUES IN SEQ ID NO: (1)..(110)

<400> SEQUENCE: 3
cctgtgcaga gattattttt taaaaggtca caatcaacat tcattgctgt cggtgggttg    60
aactgtgtgg acaagctcac tgaacaatga atgcaactgt ggccccgctt              110

<210> SEQ ID NO 4
<211> LENGTH: 89
<212> TYPE: DNA
<213> ORGANISM: Homo sapiens
<300> PUBLICATION INFORMATION:
<308> DATABASE ACCESSION NUMBER: NCBI/NR_029782
<309> DATABASE ENTRY DATE: 2014-02-27
<313> RELEVANT RESIDUES IN SEQ ID NO: (1)..(89)

<400> SEQUENCE: 4
ctgatggctg cactcaacat tcattgctgt cggtgggttt gagtctgaat caactcactg    60
atcaatgaat gcaaactgcg gaccaaaca                                      89

<210> SEQ ID NO 5
<211> LENGTH: 110
<212> TYPE: DNA
<213> ORGANISM: Homo sapiens
<300> PUBLICATION INFORMATION:
<308> DATABASE ACCESSION NUMBER: NCBI/NR_029613
<309> DATABASE ENTRY DATE: 2014-02-27
<313> RELEVANT RESIDUES IN SEQ ID NO: (1)..(110)

<400> SEQUENCE: 5
cggaaaattt gccaagggtt tgggggaaca ttcaacctgt cggtgagttt ggcagctca     60 ggcaaaccat cgaccgttga gtggaccctg aggcctggaa ttgccatcct               110

<210> SEQ ID NO 6
<211> LENGTH: 137
<212> TYPE: DNA
<213> ORGANISM: Homo sapiens
<300> PUBLICATION INFORMATION:
<308> DATABASE ACCESSION NUMBER: NCBI/NR_030179
<309> DATABASE ENTRY DATE: 2014-02-27
<313> RELEVANT RESIDUES IN SEQ ID NO: (1)..(137)

-continued

```
<400> SEQUENCE: 6
gtcccctccc ctaggccaca gccgaggtca caatcaacat tcattgttgt cggtgggttg      60
tgaggactga ggccagaccc accgggggat gaatgtcact gtggctgggc cagacacggc    120
ttaaggggaa tggggac                                                   137
```

IMMUNOMODULATION BY CONTROLLING EXPRESSION LEVELS OF MICRORNAS IN DENDRITIC CELLS

CROSS-REFERENCE TO RELATED APPLICATION

This application claims benefit under 35 U.S.C. §119(e) of provisional application 62/024,332, filed Jul. 14, 2014, which is hereby incorporated by reference in its entirety.

STATEMENT REGARDING FEDERALLY SPONSORED RESEARCH OR DEVELOPMENT

This invention was made with Government support under contract DK94548 awarded by the National Institutes of Health. The Government has certain rights in this invention.

TECHNICAL FIELD

The present invention pertains generally to immunomodulation by controlling expression levels of microRNAs in dendritic cells. In particular, the invention relates to modified dendritic cells and methods of using such dendritic cells in cellular therapy for treating various immune conditions and diseases, including transplant rejection, inflammatory disorders, autoimmune diseases, allergies, infectious diseases, immunodeficiency, and cancer.

BACKGROUND

Dendritic cells (DC) are antigen (Ag) presenting cells (APC) that initiate and regulate immune responses depending upon their state of differentiation (Banchereau et al. (2000) Annu. Rev. Immunol. 18:767-811). In transplantation, donor and recipient DC are known to be key initiators of anti-graft immune responses. Donor DC have been implicated in initiation of acute graft rejection by priming host T cells through the direct pathway of allorecognition while host DC promote chronic rejection by cross-presenting donor Ag to host T cells (Lechler et al. (2001) Immunity 14:357-368). There has been great interest in using DC to induce peripheral tolerance after organ transplantation (Morelli et al. (2007) Nat. Rev. Immunol. 7:610-621; van Kooten et al. (2011) Transplantation 91(1):2-7). Adoptive transfer of immature dendritic cells (imDC) in transplant (Tx) models has been shown to prolong graft survival (Lu et al. (1995) Transplantation 60:1539-1545; Fu et al. (1996) Transplantation 62:659-665; Lutz et al. (2000) Eur. J. Immunol. 30(7):1813-1822).

Activation of T cells requires both major histocompatibility complex (MHC)-antigen peptide recognition by the T cell receptor and costimulation by APC. Freshly-isolated imDC fail to activate T cells due to low expression of MHC and costimulatory molecules. The nature of the stimulation (e.g., inflammatory cytokines, bacterial/viral constituents, or T cell products) or the environment in which DC are stimulated (e.g., liver) may influence the type of T cell response induced (e.g., T helper (Th)1, Th2, Th17, and regulatory T (Treg)). Treg cells include CD4$^+$, CD25$^+$ (IL-2 receptor α-chain) and transcription factor forkhead box P3 (FOXP3)$^+$ and are naturally present in the immune system. They are required to maintain self-tolerance and regulate immune homeostasis. They are able to suppress the activation, proliferation and effector functions of numerous immune cells, including DC.

The function of hepatic dendritic cells (HDC) is particularly interesting given their unique function compared to DC from other sites. HDC monitor portal blood which is rich in gut-derived Ag and bacterial products such as lipopolysaccharide (LPS). These DC are therefore specialized to distinguish foreign pathogens from self or food Ag and to instigate tolerance or the appropriate immune response.

The microenvironment within which HDC reside and are activated also plays an important role. The liver is rich in immunomodulatory cytokines interleukin (IL)-10 and transforming growth factor (TGF)-β which likely have important influences on activation and function of HDC (Lee et al. (1998) Transplantation 66:1810-1817; Takayama et al. (1998) Transplantation 66:1567-1574). The allostimulatory activity of imHDC for memory T cells is refractory to pro-inflammatory cytokines, but adding Ag to immature HDC induces upregulation of MHC II, costimulatory molecules, and T cell allostimulatory activity (Abe et al. (2001) J. Hepatol. 34:61-67). In vivo administration of murine imHDC to allogeneic recipients selectively increases IL-10 production in secondary lymphoid tissue (Khanna et al. (2000) J. Immunol. 164:1346-1354). Moreover, it has been shown that HDC promote CD4 T cell hyporesponsiveness and increased Treg (Bamboat et al. (2009) J. Immunol. 182:1901-1911). Plasmacytoid (p)DC are type-1 interferon (IFN)-producing cells that have been identified in humans (Siegal et al. (1999) Science 284:1835-1837; Cella et al. (1999) Nat. Med. 5:919-923) and mice (Bjorck et al. (2001) Blood 98:3520-3526; Asselin-Paturel et al. (2001) Nat. Immunol. 2:1144-1150; Nakano et al. (2001) J. Exp. Med. 194:1171-1178) as a subset of DC which can induce tolerance (Matta et al. (2010) Eur. J. Immunol. 40:2667-2676). Studies of HDC show a higher frequency of pDC in the liver compared to the spleen (Pillarisetty et al. (2004) J. Immunol. 172:1009-1017).

Micro-ribonucleic acid (miRNA, miR) are short RNA molecules, typically 15-22 nucleotides in length, which can post-transcriptionally regulate messenger RNA transcripts, resulting in translational repression or upregulation (Anglicheau et al. (2010) Transplantation 90:105-112). Currently, miRNA antagonists or mimics are being used therapeutically in cancer and other diseases, such as inflammation and cardiovascular disease (Kasinski et al. (2011) Nat. Rev. Cancer 11:849-864; van Rooij et al. (2012) Nat. Rev. Drug Discov. 11:860-872).

There remains a need in the art for better methods of controlling immune responses for treating immune diseases and conditions, such as transplant rejection, inflammatory disorders, autoimmune diseases, allergies, infectious diseases, immunodeficiency, and cancer.

SUMMARY

The invention relates to compositions and methods of modulating an immune response by controlling levels of microRNAs in dendritic cells. In particular, the invention relates to modified dendritic cells having altered levels of miR-181 expression or activity and methods of using such dendritic cells in cellular therapy for treating various immune diseases and conditions, including transplant rejection, inflammatory disorders, autoimmune diseases, allergies, infectious diseases, immunodeficiency, and cancer.

By "miR-181" is meant any microRNA of the miR-181 family, including miR-181a (e.g., miR181a-1, miR181a-2), miR-181b (e.g., miR181b-1, miR181b-2), miR-181c, and miR-181d. In one embodiment, the miR-181 comprises a sequence selected from the group consisting of SEQ ID NOS:1-6.

In one aspect, the invention includes a method of increasing immune tolerance in a subject, the method comprising administering a therapeutically effective amount of a composition comprising tolerogenic dendritic cells to the subject. In one embodiment, the tolerogenic dendritic cells are modified dendritic cells comprising a miR-181 or miR-181 mimic. This method may be used to treat a subject for a disease or condition in which increasing immune tolerance is beneficial, such as, but not limited to, an inflammatory condition, an allergy, an autoimmune disorder, or transplant rejection. In certain embodiments, the composition comprising tolerogenic dendritic cells is administered intravenously, intra-arterially, or intralesionally. In other embodiments, the composition comprising tolerogenic dendritic cells is administered locally at the site of a tissue or organ transplant or at the site of inflammation.

In certain embodiments, the miR-181 or miR-181 mimic is provided by a recombinant polynucleotide comprising a promoter operably linked to a polynucleotide encoding the miR-181 or miR-181 mimic. The polynucleotide may comprise one or more sequences from any miR-181 allele capable of increasing immunological tolerance of dendritic cells, including any microRNA of the miR-181 family, such as miR-181a (e.g., miR181a-1, miR181a-2), miR-181b (e.g., miR181b-1, miR181b-2), miR-181c, or miR-181d. The recombinant polynucleotide may further comprise an expression vector, for example, a bacterial plasmid vector or a viral expression vector, such as, but not limited to, an adenovirus, retrovirus (e.g., γ-retrovirus and lentivirus), poxvirus, adeno-associated virus, baculovirus, or herpes simplex virus vector.

In one embodiment, the invention includes a method of treating a subject to avoid transplant rejection, the method comprising administering a therapeutically effective amount of a composition comprising tolerogenic dendritic cells comprising miR-181 or a miR-181 mimic to the subject. In order to prolong the survival of a tissue or organ transplant and avoid transplant rejection, the method may be performed prior to performance of the transplant, in conjunction with the transplant, or after the subject has received the transplant. In one embodiment, the method is performed within at least two weeks after the transplant.

In another aspect, the invention includes a method of enhancing an immune response in a subject, the method comprising administering a therapeutically effective amount of a composition comprising immunogenic dendritic cells to the subject. In one embodiment, the immunogenic dendritic cells are modified dendritic cells comprising an inhibitor of miR-181. This method may be used to treat a subject for a disease or condition in which enhancing an immune response is beneficial, such as, but not limited to, cancer, an infectious disease (e.g. caused by a pathogen, such as a virus, bacterium, protist, or fungus), or immunodeficiency. In certain embodiments, the composition comprising immunogenic dendritic cells is administered intravenously, intra-arterially, or intralesionally. In other embodiments, the composition comprising immunogenic dendritic cells is administered locally at the site of a tumor or infection. In one embodiment, the method further comprises administering an antiviral agent, an antibiotic, an antifungal agent, or an antiparasitic agent. In another embodiment, the method further comprises administering a chemotherapeutic agent. In yet another embodiment, the method further comprises administering a vaccine to the subject.

In certain embodiments, the inhibitor of miR-181 selectively binds to one or more microRNAs of the miR-181 family selected from the group consisting of miR-181a, miR-181b, miR-181c, and miR-181d. In one embodiment, the inhibitor of miR-181 binds to a miR-181 comprising a sequence selected from the group consisting of SEQ ID NOS:1-6. In certain embodiments, the inhibitor of miR-181 is selected from the group consisting of an antagomir, an antisense oligonucleotide, and an inhibitory RNA (e.g., microRNA (miRNA), a small interfering RNA (siRNA), a short hairpin RNAs (shRNA), a piwi-interacting RNA (piRNA), or a small nuclear RNA (snRNA)).

In certain embodiments, the inhibitor of miR-181 is provided by a recombinant polynucleotide comprising a promoter operably linked to a polynucleotide encoding the inhibitor of miR-181. The recombinant polynucleotide may comprise an expression vector, for example, a bacterial plasmid vector or a viral expression vector, such as, but not limited to, an adenovirus, retrovirus (e.g., γ-retrovirus and lentivirus), poxvirus, adeno-associated virus, baculovirus, or herpes simplex virus vector.

In another aspect, the invention includes a host dendritic cell transfected with miR-181 or a miR-181 mimic. In one embodiment, the miR-181 or miR-181 mimic is provided by a recombinant polynucleotide comprising a promoter operably linked to a polynucleotide sequence encoding the miR-181 or the miR-181 mimic. In one embodiment, the dendritic cell is a plasmacytoid dendritic cell or a myeloid dendritic cell. The dendritic cell may be isolated from any bodily fluid, tissue, or organ comprising dendritic cells, including, but not limited to, blood, liver, skin, synovial tissue, interstitial tissues, nose, lungs, stomach, intestines, bone marrow, lymph nodes, thymus, spleen, or another hematopoietic or lymphoid organ.

In another aspect, the invention includes a composition comprising tolerogenic dendritic cells comprising a miR-181 or miR-181 mimic. The composition may comprise plasmacytoid dendritic cells (pDC) or myeloid dendritic cells (mDC), or a combination thereof. In one embodiment, at least 85-100% of the dendritic cells in the composition are tolerogenic dendritic cells, including any percent identity within this range, such as 85, 86, 87, 88, 89, 90, 91, 92, 93, 94, 95, 96, 97, 98, 99, or 100% of the dendritic cells in the composition are tolerogenic dendritic cells. The composition may further comprise a pharmaceutically acceptable excipient. In certain embodiments, the composition further comprises one or more other agents for treating inflammation or suppressing an immune response, such as an immunosuppressive drug or anti-inflammatory agent.

In another aspect, the invention includes a method of producing a tolerogenic dendritic cell, the method comprising: a) transfecting a host dendritic cell with a recombinant polynucleotide comprising a polynucleotide sequence encoding a miR-181 or miR-181 mimic operably linked to a promoter; and b) culturing the transfected dendritic cell under conditions whereby the miR-181 or miR-181 mimic is expressed.

In another aspect, the invention includes a host dendritic cell transfected with an inhibitor of miR-181. In certain embodiments, the inhibitor of miR-181 selectively binds to one or more microRNAs of the miR-181 family selected from the group consisting of miR-181a, miR-181b, miR-181c, and miR-181d. In one embodiment, the inhibitor of miR-181 binds to a miR-181 comprising a sequence selected from the group consisting of SEQ ID NOS:1-6. The inhibitor of miR-181 may be an antagomir, an antisense oligonucleotide, or an inhibitory RNA (e.g., a miRNA, an siRNA, an shRNA, a piRNA, or an snRNA). In one embodiment, the inhibitor of miR-181 is provided by a recombinant polynucleotide comprising a promoter operably linked to a polynucleotide sequence encoding the inhibitor of miR-181.

In another aspect, the invention includes a composition comprising immunogenic dendritic cells comprising an inhibitor of miR-181. The composition may comprise plasmacytoid dendritic cells (pDC) or myeloid dendritic cells (mDC), or a combination thereof. In one embodiment, at least 85-100% of the dendritic cells in the composition are immunogenic dendritic cells, including any percent identity within this range, such as 85, 86, 87, 88, 89, 90, 91, 92, 93, 94, 95, 96, 97, 98, 99, or 100% of the dendritic cells in the composition are immunogenic dendritic cells. The composition may further comprise a pharmaceutically acceptable excipient. In certain embodiments, the composition further comprises one or more other agents for treating an infection or cancer, including, but not limited to, an antiviral agent, an antibiotic, an antifungal agent, an antiparasitic agent, or a chemotherapeutic agent. In one embodiment, the composition further comprises a vaccine against cancer or an infection.

In another aspect, the invention includes a method of producing an immunogenic dendritic cell, the method comprising: a) transfecting a host dendritic cell with a recombinant polynucleotide comprising a polynucleotide sequence encoding an inhibitor of miR-181 operably linked to a promoter; and b) culturing the transfected dendritic cell under conditions whereby the inhibitor of miR-181 is expressed.

In another aspect, the invention includes a method of adoptive cellular immunotherapy for enhancing immune tolerance, the method comprising: a) collecting a sample comprising dendritic cells from a subject; b) transfecting the dendritic cells ex vivo with a miR-181 or miR-181 mimic; and c) administering a therapeutically effective amount of the transfected dendritic cells to the subject. The method may further comprise culturing the dendritic cells under conditions in which the dendritic cells proliferate before transfer to the subject. In certain embodiments, the transfected dendritic cells are administered intravenously, intra-arterially, or intralesionally. In other embodiments, the transfected dendritic cells are administered locally at the site of a tissue or organ transplant or at the site of inflammation. Multiple cycles of adoptive cellular immunotherapy may be administered to the subject.

In certain embodiments, adoptive cellular immunotherapy is performed to treat a subject to avoid transplant rejection. In certain embodiments, the method may be performed prior to performance of the transplant, in conjunction with the transplant, or after the subject has received the transplant. In one embodiment, the method is performed within at least two weeks after the transplant. Preferably, the transfected dendritic cells are administered in an amount sufficient to prolong survival of a transplanted organ or tissue.

In other embodiments, adoptive cellular immunotherapy is performed to treat a subject for an inflammatory condition or an autoimmune disorder. Preferably, the transfected dendritic cells are administered in an amount sufficient to reduce inflammation in the subject.

In another aspect, the invention includes a method of adoptive cellular immunotherapy for enhancing an immune response, the method comprising:
a) collecting a sample comprising dendritic cells from a subject; b) transfecting the dendritic cells ex vivo with an inhibitor of miR-181; and c) administering a therapeutically effective amount of the transfected dendritic cells to the subject. The method may further comprise culturing the dendritic cells under conditions in which the dendritic cells proliferate before transfer to the subject. In certain embodiments, the transfected dendritic cells are administered intravenously, intra-arterially, or intralesionally. In other embodiments, the transfected dendritic cells are administered locally at the site of a tumor or infection. Multiple cycles of adoptive cellular immunotherapy may be administered to the subject.

In certain embodiments, adoptive cellular immunotherapy is performed to treat a subject for cancer. Multiple cycles of adoptive cellular immunotherapy may be administered to the subject for a time period sufficient to effect at least a partial tumor response or, more preferably, a complete tumor response. The method may further comprise administering a chemotherapeutic agent to the subject. In one embodiment, the transfected dendritic cells are administered locally at the site of cancerous cells or a tumor.

In other embodiments, adoptive cellular immunotherapy is performed to treat a subject for an infection. Multiple cycles of adoptive cellular immunotherapy may be administered to the subject for a time period sufficient to eradicate the infection. The method may further comprise administering an antiviral agent, an antibiotic, an antifungal agent, or an antiparasitic agent. Additionally, the method may further comprise administering a vaccine. In one embodiment, the transfected dendritic cells are administered locally at the site of infection.

In yet another aspect, the invention provides kits comprising at least one miR-181, miR-181 mimic, or miR-181 inhibitor, or a recombinant nucleic acid encoding a miR-181, miR-181 mimic, or miR-181 inhibitor, and dendritic cells (e.g., either already transfected or separately). The kit may also include one or more transfection reagents to facilitate delivery of oligonucleotides or polynucleotides to the dendritic cells. The kit may further contain means for administering dendritic cells to a subject. The kit may also comprise instructions for treating a subject with dendritic cells. For example, the kit may comprise instructions for administering dendritic cells transfected with a miR-181 or miR-181 mimic or a recombinant polynucleotide encoding a miR-181 or miR-181 mimic to a subject for treating a condition or disease that would benefit from increased immune tolerance. Alternatively, the kit may comprise instructions for administering dendritic cells transfected with a miR-181 inhibitor or a recombinant polynucleotide encoding a miR-181 inhibitor to a subject for treating a condition or disease that would benefit from an enhanced immune response.

These and other embodiments of the subject invention will readily occur to those of skill in the art in view of the disclosure herein.

BRIEF DESCRIPTION OF THE FIGURES

FIG. 2A shows results from intravenous injection of $5\times10^5$-$2\times10^6$ DC into recipient BALB/cJ mice seven days prior to heterotopic cardiac allograft transplant using WT C57BL/6J donor hearts. P-values were determined using the Mantel-Cox log rank test. FIG. 2B shows results from quantitative polymerase chain reaction performed for miR-181a. Results are from 5-7 samples with p-values determined using Student's unpaired t-test.

FIG. 3A shows 5-9 experiments per group.*p<0.01, one sample t-test, and p<0.05, Wilcoxon sign rank test; **p<0.01, one sample t-test, and NS by Wilcoxon sign rank test). FIG. 3B shows results from mice that were injected 16 hours prior to isolation of liver pDC with 100 μg i.v. of TLR9 ligand, CpG A ODN2216. Flow cytometric analyses were performed as in FIG. 3A. 3 samples per group with p values determined by one-sample t-test.

DETAILED DESCRIPTION

Figure 1A:
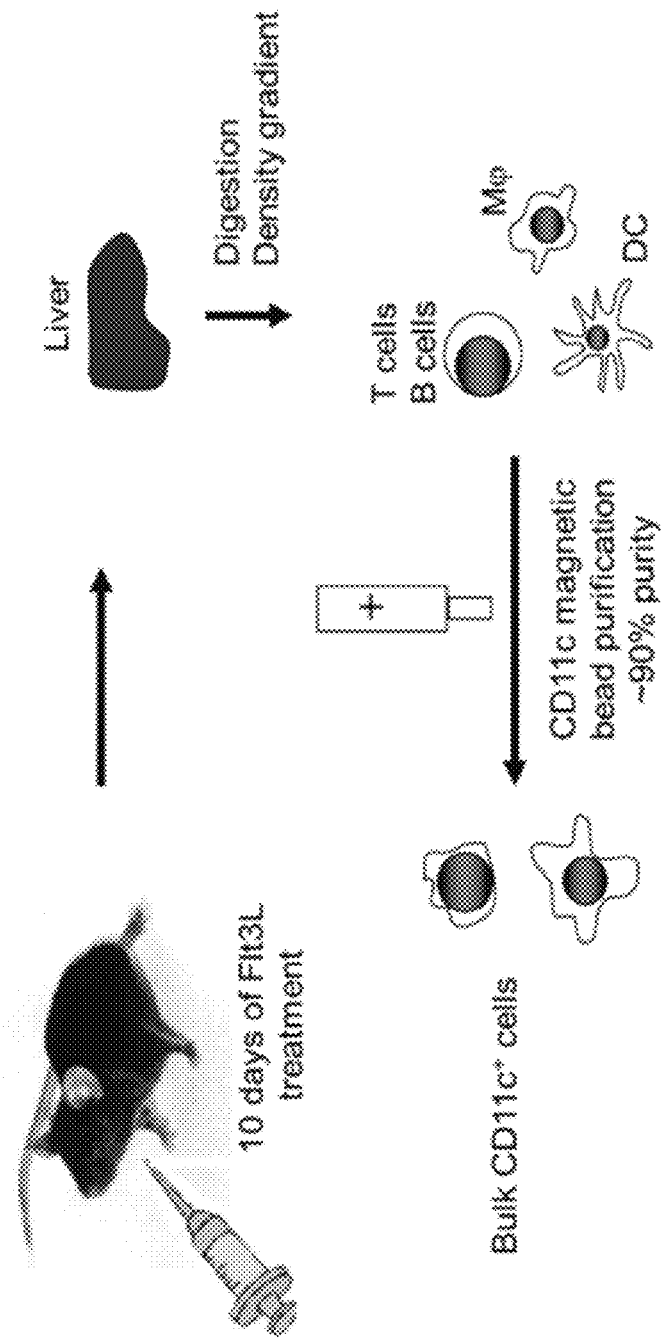
FIGS. 1A-1C show a schematic of the experimental design, including isolation of dendritic cells (FIG. 1A), flow sorting of dendritic cells (FIG. 1B), and adoptive transfer and transplant (FIG. 1C).
Figure 1B:
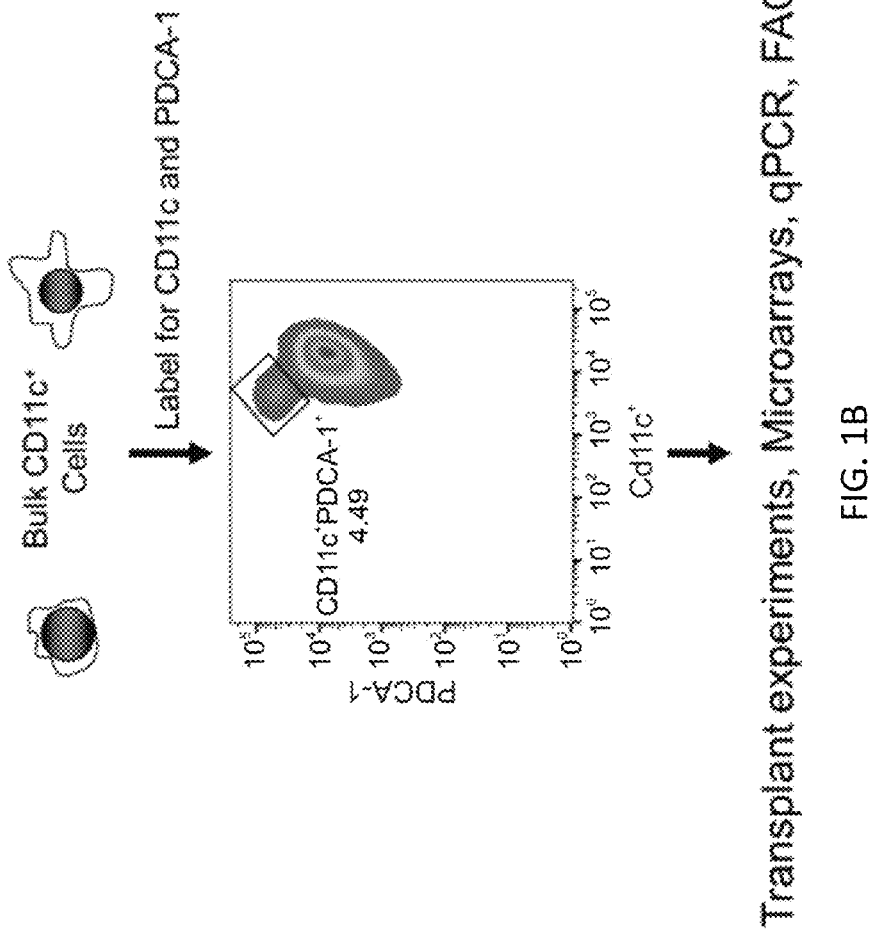
Figure 1C:
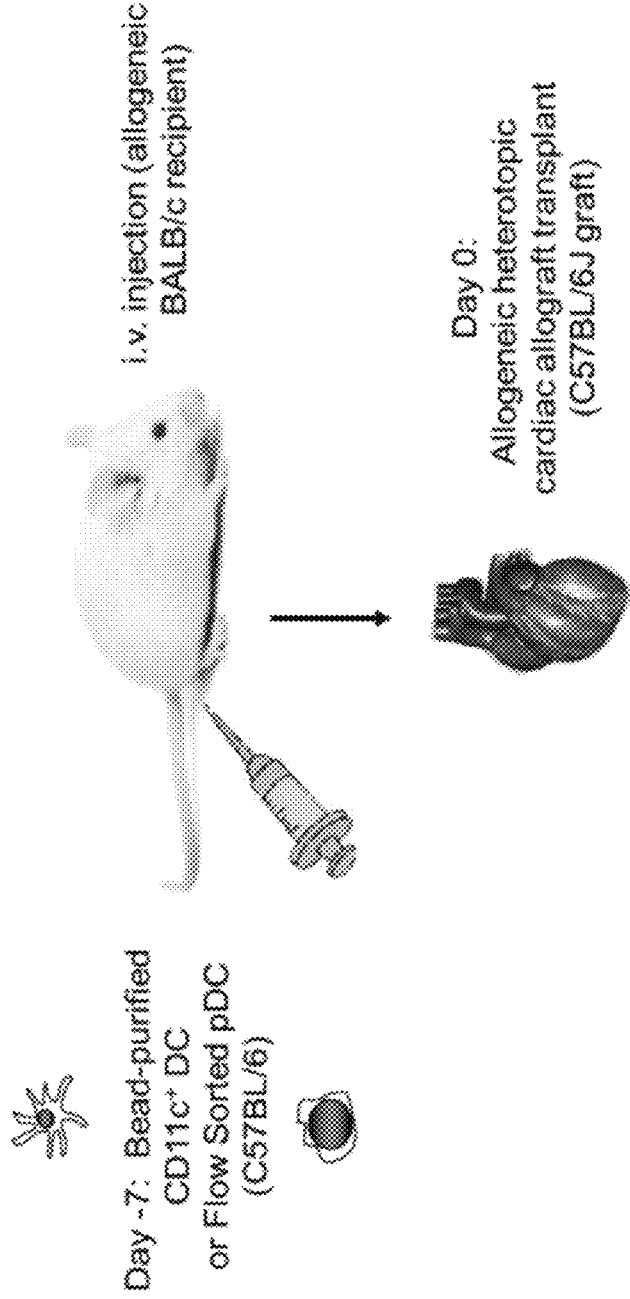

The practice of the present invention will employ, unless otherwise indicated, conventional methods of pharmacology, chemistry, biochemistry, recombinant DNA techniques and immunology, within the skill of the art. Such techniques are explained fully in the literature. See, e.g., *Macrophages and Dendritic Cells: Methods and Protocols* (Methods in Molecular Biology, N. E. Reiner ed., Humana Press, 2009); *Dendritic Cells, 2nd edition: Biology and Clinical Applications* (M. T. Lotze and A. W. Thomson eds., Academic Press, 2$^{nd}$ edition, 2001); *siRNA Design: Methods and Protocols* (Methods in Molecular Biology, D. J. Taxman ed., Humana Press, 2013); *siRNA and miRNA Gene Silencing: From Bench to Bedside* (Methods in Molecular Biology, M. Sioud ed., Humana Press, 2009); *RNA Interference* (Current Topics in Microbiology and Immunology, P. J. Paddison and P. K. Vogt eds., Springer, 1$^{st}$ edition, 2008); *Handbook of Experimental Immunology*, Vols. I-IV (D. M. Weir and C. C. Blackwell eds., Blackwell Scientific Publications); A. L. Lehninger, *Biochemistry* (Worth Publishers, Inc., current addition); Sambrook, et al., *Molecular Cloning: A Laboratory Manual* (3$^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a dendritic cell" includes a mixture of two or more dendritic cells, and the like.

The term "about," particularly in reference to a given quantity, is meant to encompass deviations of plus or minus five percent.

"Immunogenic" means capable of inducing an adaptive immunological response.

"Tolerogenic" means capable of suppressing or down-modulating an adaptive immunological response.

The term "immunogenic dendritic cell" refers to a dendritic cell that has the ability to induce an adaptive immunological response. An immunogenic dendritic cell has the ability to activate effector T cells. Immunogenic dendritic cells typically show high expression levels of the surface receptors HLA-DR, CD40, CD80, CD83 and CD86.

The term "tolerogenic dendritic cell" refers to a dendritic cell that has the ability to induce immunological tolerance. A tolerogenic dendritic cell has low ability to activate effector T cells but high ability to induce and activate regulatory T cells. Tolerogenic dendritic cells generally have lower surface expression of major histocompatibility complex class II (MHC II) and costimulatory molecule CD86 than immunogenic dendritic cells.

"Immunomodulating" or "modulating an immune response" means capable of modifying an innate or an adaptive immunological response and includes immunostimulatory as well as immunosuppressive effects.

The terms "microRNA," "miRNA," and "miR" are interchangeable and refer to endogenous or artificial non-coding RNAs that are capable of regulating gene expression. Mature microRNAs are single-stranded RNA molecules, typically about 19 to about 25 nucleotides in length (including about 19, about 20, about 21, about 22, about 23, about 24, and about 25 nucleotides), that effectively reduce the expression level of target polynucleotides and polypeptides through the RNA interference (RNAi) pathway (i.e., through association with the RNA-induced silencing complex (RISC) and subsequent degradation of target mRNA or translational inhibition).

The terms "miR-181" and "microRNA-181" refer to any microRNA of the miR-181 family, including miR-181a (e.g., miR181a-1, miR181a-2), miR-181b (e.g., miR181b-1, miR181b-2), miR-181c, and miR-181d. A number of miR-181 nucleic acid sequences are known. Representative miR-181 sequences are presented in SEQ ID NOS:1-6 and additional representative sequences are listed in the National Center for Biotechnology Information (NCBI) database. See, for example, NCBI entries: Accession Nos. NR_029626, NR_029611, NR_029612, NR_029782, NR_029613, NR_030179, NR_029568, NR_105137, NR_034644, NR_033048, NR_032219, NR_031898, NR_031926, NR_029795, NR_029820, NR_106591, NR_105138, NR_105337, NR_034645, NR_033049, NR_032220, NR_029820, AY866298, AY866297, AY866295, AY866294, AY866293, AY866292, AY866173, AY866172, AY866171, AY866170, NR_032034, NR_106572, NR_106246, NR_105139, NR_031372, NR_038494, NR_034781, NR_032033, NR_032186, NR_031897, NR_035690, NR_105140, NR_106313, NR_031181, NR_038535, NR_032428, and NR_029602; all of which sequences (as entered by the date of filing of this application) are herein incorporated by reference. Any of these sequences or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the variant has miR-181 biological activity, can be used to modulate an immune response as described herein.

The terms "small interfering RNA" and "siRNA" refer to double-stranded RNA molecules, comprising a sense strand and an antisense strand, having sufficient complementarity to one another to form a duplex. Such sense and antisense strands each have a region of complementarity ranging, for example, from about 10 to about 30 contiguous nucleotides that base pair sufficiently to form a duplex or double-stranded siRNA. Such siRNAs are able to specifically interfere with the expression of a gene by triggering the RNAi machinery (e.g., RISC) of a cell to remove RNA transcripts having identical or homologous sequences to the siRNA sequence. As described herein, the sense and antisense strands of an siRNA may each consist of only complementary regions, or one or both strands may comprise additional sequences, including non-complementary sequences, such as 5' or 3' overhangs. An overhang may be of any length of nonhomologous residues, for example, 2, 3, 4, 5, 6, 7, 8, 9, 10, 11, 12, 13, 14, 15, 16 or more nucleotides. In addition, siRNAs may have other modifications, such as, for example, substituted or modified nucleotides or other sequences, which contribute to either the stability of the siRNA, its delivery to a cell or tissue, or its potency in triggering RNAi. It is to be understood that the terms "strand" and "oligonucleotide" may be used interchangeably in reference to the sense and antisense strands of siRNA compositions.

The terms "small hairpin RNA" and "shRNA" refer to an RNA sequence comprising a double-stranded stem region and a loop region at one end forming a hairpin loop. The double-stranded region is typically about 19 nucleotides to about 30 nucleotides in length on each side of the stem, and the loop region is typically about three to about twelve nucleotides in length. The shRNA may include 3'- or 5'-terminal single-stranded overhangs. An overhang may be of any length of nonhomologous residues, for example, 2, 3, 4, 5, 6, 7, 8, 9, 10, 11, 12, 13, 14, 15, 16 or more nucleotides. In addition, such shRNAs may have other modifications, such as, for example, substituted or modified nucleotides or other sequences, which contribute to either the stability of the shRNA, its delivery to a cell or tissue, or its potency in triggering RNA interference. In some cases, the shRNA may be derived from an siRNA, the shRNA comprising the sense strand and antisense strand of the siRNA connected by a loop.

The terms "piRNA" and "Piwi-interacting RNA" are interchangeable and refer to a class of small RNAs involved in gene silencing. PiRNA molecules typically are between 26 and 31 nucleotides in length.

The terms "snRNA" and "small nuclear RNA" are interchangeable and refer to a class of small RNAs involved in a variety of processes including RNA splicing and regulation of transcription factors. The subclass of small nucleolar RNAs (snoRNAs) is also included. The term is also intended to include artificial snRNAs, such as antisense derivatives of snRNAs comprising antisense sequences directed against miR-181.

The terms "polynucleotide," "oligonucleotide," "nucleic acid" and "nucleic acid molecule" are used herein to include a polymeric form of nucleotides of any length, either ribonucleotides or deoxyribonucleotides. This term refers only to the primary structure of the molecule. Thus, the term includes triple-, double- and single-stranded DNA, as well as triple-, double- and single-stranded RNA. It also includes modifications, such as by methylation and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), any other type of polynucleotide which is an N- or C-glycoside of a purine or pyrimidine base, and other polymers containing nonnucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. There is no intended distinction in length between the terms "polynucleotide," "oligonucleotide," "nucleic acid" and "nucleic acid molecule," and these terms will be used interchangeably. Thus, these terms include, for example, 3'-deoxy-2',5'-DNA, oligodeoxyribonucleotide N3' P5' phosphoramidates, 2'-O-alkyl-substituted RNA, double- and single-stranded DNA, as well as double- and single-stranded RNA, microRNA, DNA:RNA hybrids, and hybrids between PNAs and DNA or RNA, and also include known types of modifications, for example, labels which are known in the art, methylation, "caps," substitution of one or more of the naturally occurring nucleotides with an analog (e.g., 2-aminoadenosine, 2-thiothymidine, inosine, pyrrolo-pyrimidine, 3-methyl adenosine, C5-propynylcytidine, C5-propynyluridine, C5-bromouridine, C5-fluorouridine, C5-iodouridine, C5-methylcytidine, 7-deazaadenosine, 7-deazaguanosine, 8-oxoadenosine, 8-oxoguanosine, O(6)-methylguanine, and 2-thiocytidine), internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalklyphosphoramidates, aminoalkylphosphotriesters), those containing pendant moieties, such as, for example, proteins (including nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide. The term also includes locked nucleic acids (e.g., comprising a ribonucleotide that has a methylene bridge between the 2'-oxygen atom and the 4'-carbon atom). See, for example, Kurreck et al. (2002) Nucleic Acids Res. 30: 1911-1918; Elayadi et al. (2001) Curr. Opinion Invest. Drugs 2: 558-561; Orum et al. (2001)

Curr. Opinion Mol. Ther. 3: 239-243; Koshkin et al. (1998) Tetrahedron 54: 3607-3630; Obika et al. (1998) Tetrahedron Lett. 39: 5401-5404.

The term "homologous region" refers to a region of a nucleic acid with homology to another nucleic acid region. Thus, whether a "homologous region" is present in a nucleic acid molecule is determined with reference to another nucleic acid region in the same or a different molecule. Further, since a nucleic acid is often double-stranded, the term "homologous, region," as used herein, refers to the ability of nucleic acid molecules to hybridize to each other. For example, a single-stranded nucleic acid molecule can have two homologous regions which are capable of hybridizing to each other. Thus, the term "homologous region" includes nucleic acid segments with complementary sequence. Homologous regions may vary in length, but will typically be between 4 and 40 nucleotides (e.g., from about 4 to about 40, from about 5 to about 40, from about 5 to about 35, from about 5 to about 30, from about 5 to about 20, from about 6 to about 30, from about 6 to about 25, from about 6 to about 15, from about 7 to about 18, from about 8 to about 20, from about 8 to about 15, etc.).

The term "complementary" and "complementarity" are interchangeable and refer to the ability of polynucleotides to form base pairs with one another. Base pairs are typically formed by hydrogen bonds between nucleotide units in antiparallel polynucleotide strands or regions. Complementary polynucleotide strands or regions can base pair in the Watson-Crick manner (e.g., A to T, A to U, C to G). 100% complementary refers to the situation in which each nucleotide unit of one polynucleotide strand or region can hydrogen bond with each nucleotide unit of a second polynucleotide strand or region. Less than perfect complementarity refers to the situation in which some, but not all, nucleotide units of two strands or two regions can hydrogen bond with each other and can be expressed as a percentage.

A "target site" or "target sequence" is the nucleic acid sequence recognized (i.e., sufficiently complementary for hybridization) by an antisense oligonucleotide or inhibitory RNA molecule (e.g., microRNA, siRNA, or shRNA).

The term "hairpin" and "stem-loop" can be used interchangeably and refer to stem-loop structures. The stem results from two sequences of nucleic acid or modified nucleic acid annealing together to generate a duplex. The loop lies between the two strands comprising the stem.

The term "loop" refers to the part of the stem-loop between the two homologous regions (the stem) that can loop around to allow base-pairing of the two homologous regions. The loop can be composed of nucleic acid (e.g., DNA or RNA) or non-nucleic acid material(s), referred to herein as nucleotide or non-nucleotide loops. A non-nucleotide loop can also be situated at the end of a nucleotide molecule with or without a stem structure.

"Inhibition of gene expression" refers to the absence (or observable decrease) in the level of protein and/or RNA product from a target gene. "Specificity" refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radiolmmunoassay (RIA), other immunoassays, and fluorescence activated cell analysis (FACS). For RNA-mediated inhibition in a cell line or whole organism, gene expression is conveniently assayed by use of a reporter or drug resistance gene whose protein product is easily assayed.

Depending on the assay, quantitation of the amount of gene expression allows one to determine a degree of inhibition which is greater than 10%, 33%, 50%, 90%, 95% or 99% as compared to a cell not treated with the inhibitory agent. Lower doses of the administered inhibitory agent and longer times after administration of the inhibitory agent may result in inhibition in a smaller fraction of cells (e.g., at least 10%, 20%, 50%, 75%, 90%, or 95% of targeted cells). Quantitation of gene expression in a cell may show similar amounts of inhibition at the level of accumulation of target RNA or translation of target protein. As an example, the efficiency of inhibition may be determined by assessing the amount of gene product in the cell: RNA may be detected with a hybridization probe having a nucleotide sequence outside the region used for the inhibitory, or a translated polypeptide may be detected with an antibody raised against the polypeptide sequence of that region.

"Administering" a nucleic acid, such as a microRNA, siRNA, shRNA, piRNA, snRNA, antisense nucleic acid, or lncRNA to a cell comprises transducing, transfecting, electroporating, translocating, fusing, phagocytosing, shooting or ballistic methods, etc., i.e., any means by which a nucleic acid can be transported across a cell membrane.

The term "transfection" is used to refer to the uptake of foreign DNA or RNA by a cell. A cell has been "transfected" when exogenous DNA or RNA has been introduced inside the cell membrane. A number of transfection techniques are generally known in the art. See, e.g., Graham et al. (1973) Virology, 52:456, Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA or RNA moieties into suitable host cells. The term refers to both stable and transient uptake of the genetic material, and includes uptake, for example, of microRNA, siRNA, shRNA, piRNA, lncRNA, or antisense nucleic acids.

By "selectively binds" is meant that the molecule binds preferentially to the target of interest or binds with greater affinity to the target than to other molecules. For example, an inhibitory RNA (e.g., miRNA, siRNA, or shRNA) will bind to a substantially complementary sequence and not to unrelated sequences.

"Pharmaceutically acceptable excipient or carrier" refers to an excipient that may optionally be included in the compositions of the invention and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly salts containing pharmaceutically acceptable cations include, but are not limited to, sodium, potassium, calcium, aluminum, lithium, and ammonium (including substituted ammonium).

As used herein, the term "pathogen" or "parasite" or "microbe" refers to any virus or organism that spends at least part of its life cycle or reproduces within a host. Intracellular pathogens include viruses (e.g., influenza virus, respiratory syncytial virus, hepatitis virus B, hepatitis virus C, herpes virus, papilloma virus, and human immunodeficiency virus), bacteria (e.g., *Listeria*, Mycobacteria (e.g., *Mycobacterium tuberculosis, Mycobacterium leprae*), *Salmonella* (e.g., *S. typhi*), enteropathogenic *Escherichia coli* (EPEC), enterohaemorrhagic *Escherichia coli* (EHEC), *Yersinia, Shigella, Chlamydia, Chlamydophila, Staphylococcus, Legionella*), protozoa (e.g., *Plasmodium* (e.g., *P. vivax, P. falciparum, P. ovale*, and *P. malariae*), Taxoplasma, *Leishmania*), and fungi (e.g., *Aspergillus, Blastomyces, Candida*). Eukaryotic intercellular parasites include trematodes (e.g., *Schistosoma, Clonorchis*), hookworms (e.g., *Ancylostoma duodenale* and *Necator americanus*), and tape worms (e.g., *Taenia solium, T. saginata, Diphyllobothrium* spp., *Hymenolepis* spp., *Echinococcus* spp.).

The terms "tumor," "cancer" and "neoplasia" are used interchangeably and refer to a cell or population of cells whose growth, proliferation or survival is greater than growth, proliferation or survival of a normal counterpart cell, e.g. a cell proliferative, hyperproliferative or differentiative disorder. Typically, the growth is uncontrolled. The term "malignancy" refers to invasion of nearby tissue. The term "metastasis" or a secondary, recurring or recurrent tumor, cancer or neoplasia refers to spread or dissemination of a tumor, cancer or neoplasia to other sites, locations or regions within the subject, in which the sites, locations or regions are distinct from the primary tumor or cancer. Neoplasia, tumors and cancers include benign, malignant, metastatic and non-metastatic types, and include any stage (I, II, III, IV or V) or grade (G1, G2, G3, etc.) of neoplasia, tumor, or cancer, or a neoplasia, tumor, cancer or metastasis that is progressing, worsening, stabilized or in remission. In particular, the terms "tumor," "cancer" and "neoplasia" include carcinomas, such as squamous cell carcinoma, adenocarcinoma, adenosquamous carcinoma, anaplastic carcinoma, large cell carcinoma, and small cell carcinoma. These terms include, but are not limited to, breast cancer, prostate cancer, lung cancer, ovarian cancer, bladder cancer, testicular cancer, colon cancer, pancreatic cancer, gastric cancer, hepatic cancer, leukemia, lymphoma, adrenal cancer, thyroid cancer, pituitary cancer, renal cancer, brain cancer, skin cancer, head cancer, neck cancer, oral cavity cancer, tongue cancer, and throat cancer.

An "effective amount" of a composition comprising tolerogenic dendritic cells (e.g., dendritic cells transfected with a miR-181 or miR-181 mimic) is an amount sufficient to effect beneficial or desired results, such as an amount that increases immune tolerance. An effective amount can be administered in one or more administrations, applications, or dosages.

An "effective amount" of a composition comprising immunogenic dendritic cells (e.g., dendritic cells transfected with an inhibitor of miR-181) is an amount sufficient to effect beneficial or desired results, such as an amount that enhances an immune response. An effective amount can be administered in one or more administrations, applications, or dosages.

By "anti-tumor activity" is intended a reduction in the rate of cell proliferation, and hence a decline in growth rate of an existing tumor or in a tumor that arises during therapy, and/or destruction of existing neoplastic (tumor) cells or newly formed neoplastic cells, and hence a decrease in the overall size of a tumor during therapy. Such activity can be assessed using animal models.

By "therapeutically effective dose or amount" of a composition comprising tolerogenic dendritic cells (e.g., dendritic cells transfected with a miR-181 or miR-181 mimic) is intended an amount that, when administered as described herein, brings about a positive therapeutic response, such as improved recovery from an inflammatory condition, an allergy, or an autoimmune disorder, or better graft tolerance. Improved recovery may include a reduction in inflammation, pain, or autoimmune-induced tissue damage, or prolonged survival of transplanted tissue or organs. Additionally, a therapeutically effective dose or amount may reduce the need for immunosuppressive or anti-inflammatory drugs. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

By "therapeutically effective dose or amount" of a composition comprising immunogenic dendritic cells (e.g., dendritic cells transfected with an inhibitor of miR-181) is intended an amount that, when administered as described herein, brings about a positive therapeutic response, such as improved recovery from cancer, an infection, or immunodeficiency. Improved recovery may include enhanced immunity or eradication of an infectious pathogen. Additionally, a therapeutically effective dose or amount may have anti-tumor activity. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

"Substantially purified" generally refers to isolation of a substance (compound, polynucleotide, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353 358, National biomedical Research Foundation, Washington, D.C., which adapts the local homology algorithm of Smith and Waterman Advances in Appl. Math. 2:482 489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non redundant, GenBank+EMBL+DDBJ+PDB+ GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells", "host cells," "cells", "cell lines," "cell cultures", and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

"Operably linked" refers to an arrangement of elements wherein the components so described are configured so as to perform their usual function. Thus, a given promoter operably linked to a coding sequence is capable of effecting the expression of the coding sequence when the proper enzymes are present. Expression is meant to include the transcription of any one or more of transcription of a microRNA, siRNA, shRNA, piRNA, snRNA, lncRNA, antisense nucleic acid, or mRNA from a DNA or RNA template and can further include translation of a protein from an mRNA template. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

The terms "variant" refers to biologically active derivatives of the reference molecule that retain desired activity, such as gene regulatory activity, RNA interference (RNAi), or transcription factor activity. In general, the term "variant" refers to molecules (e.g., miRNAs, siRNAs, shRNAs, piRNAs, snRNAs, lncRNAs, or antisense nucleic acids) having a native sequence and structure with one or more additions, substitutions (generally conservative in nature) and/or deletions, relative to the native molecule, so long as the modifications do not destroy biological activity and which are "substantially homologous" to the reference molecule. In general, the sequences of such variants will have a high degree of sequence homology to the reference sequence, e.g., sequence homology of more than 50%, generally more than 60%-70%, even more particularly 80%-85% or more, such as at least 90%-95% or more, when the two sequences are aligned.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses.

The term "derived from" is used herein to identify the original source of a molecule but is not meant to limit the method by which the molecule is made which can be, for example, by chemical synthesis or recombinant means.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, particularly in a human, and includes: (a) increasing survival time; (b) decreasing the risk of death due to the disease; (c) preventing the disease from occurring in a subject which may be predisposed to the disease but has not yet been diagnosed as having it; (d) inhibiting the disease, i.e., arresting its development (e.g., reducing the rate of disease progression); and (e) relieving the disease, i.e., causing regression of the disease.

The terms "subject," "individual," and "patient," are used interchangeably herein and refer to any mammalian subject for whom diagnosis, prognosis, treatment, or therapy is desired, particularly humans. Other subjects may include cattle, dogs, cats, guinea pigs, rabbits, rats, mice, horses, and so on. In some cases, the methods of the invention find use in experimental animals, in veterinary application, and in the development of animal models for disease, including, but not limited to, rodents including mice, rats, and hamsters; primates, and transgenic animals.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery that levels of expression of miR-181 family microRNAs (e.g., miR-181a, miR-181b, miR-181c, and miR-181d) control whether dendritic cells are tolerogenic or immunogenic (see Examples 1 and 3). Accordingly, an immune response can be modulated by modifying dendritic cells to alter their level of expression or activity of one or more microRNAs of the miR-181 family. Modified dendritic cells having increased levels of a miR-181 can be used to suppress a cellular immune response, whereas modified dendritic cells having decreased levels of a miR-181 can be used to enhance an immune response. Such modified dendritic cells can be used in immunotherapy to treat various immune conditions and diseases, including transplant rejection, inflammatory conditions, autoimmune diseases, allergies, infections, immunodeficiency, and cancer.

In order to further an understanding of the invention, a more detailed discussion is provided below regarding modified dendritic cells having altered levels of miR-181 and therapeutic uses for such dendritic cells in modulating immune responses for treatment of various immune conditions and diseases.

A. Modified Dendritic Cells

The present invention pertains generally to compositions comprising modified dendritic cells having altered levels of miR-181 expression or activity and methods of using such dendritic cells to modulate an immune response for treatment of various immune diseases and conditions. Dendritic cells that have been transfected with a miR-181 or miR-181 mimic (i.e., polynucleotide that mimics miR-181 function) have tolerogenic properties and are useful for treating immune diseases and conditions benefitting from increased immunological tolerance, including, but not limited to, inflammatory conditions, autoimmune diseases, allergies, and transplant rejection. Conversely, dendritic cells that have been transfected with an inhibitor of miR-181 have immunogenic properties and are useful for treating immune diseases and conditions benefitting from an enhanced immunological response, including, but not limited to, infections, immunodeficiency, and cancer.

In certain embodiments, dendritic cells comprising a miR-181 or miR-181 mimic are used in the practice of the invention to increase immunological tolerance in a subject. The miR-181 or miR-181 mimic may be synthetically or recombinantly produced and can be provided by a polynucleotide comprising the miR-181 or miR-181 mimic sequence. The polynucleotide may comprise one or more sequences from any miR-181 allele capable of increasing immunological tolerance of dendritic cells, including any microRNA of the miR-181 family, such as miR-181a (e.g., miR181a-1, miR181a-2), miR-181b (e.g., miR181b-1, miR181b-2), miR-181c, or miR-181d. In certain embodiments, the polynucleotide comprises a sequence selected from the group consisting of SEQ ID NOS:1-6 or a variant thereof displaying at least about 80-100% sequence identity thereto, including any percent identity within this range, such as 81, 82, 83, 84, 85, 86, 87, 88, 89, 90, 91, 92, 93, 94, 95, 96, 97, 98, 99% sequence identity thereto, wherein the polynucleotide retains miR-181 biological function (e.g., confers tolerogenic properties on dendritic cells). The polynucleotide can be single stranded or double stranded and may contain one or more chemical modifications, such as, but not limited to, locked nucleic acids, peptide nucleic acids, sugar modifications, such as 2'-O-alkyl (e.g., 2'-O-methyl, 2'-O-methoxyethyl), 2'-fluoro, and 4'-thio modifications, and backbone modifications, such as one or more phosphorothioate, morpholino, or phosphonocarboxylate linkages. In one embodiment, the polynucleotide is conjugated to cholesterol. In certain embodiments, the miR-181 or miR-181 mimic is provided by a recombinant polynucleotide comprising a sequence encoding the miR-181 or miR-181 mimic operably linked to a promoter. In certain embodiments, the amount and/or activity of miR-181 in a dendritic cell may be increased by at least 10%, 20%, 50%, 100%, 200%, 500%, or 10-fold, 20-fold, 50-fold, or more by such a recombinant polynucleotide.

In one embodiment, the invention includes a method of modulating an immune response in a subject, the method comprising administering a therapeutically effective amount of a composition comprising tolerogenic dendritic cells (e.g., dendritic cells transfected with a miR-181 or miR-181 mimic, or a recombinant polynucleotide encoding them) to the subject, wherein the tolerogenic dendritic cells are administered in an amount sufficient to increase immunological tolerance in the subject. A "therapeutically effective dose or amount" of a composition comprising tolerogenic dendritic cells (e.g., dendritic cells transfected with a miR-181 or miR-181 mimic, or recombinant polynucleotide encoding them) is intended an amount that, when administered as described herein, brings about a positive therapeutic response, such as improved recovery from an inflammatory condition, an allergy, or an autoimmune disorder, or better graft tolerance. Improved recovery may include a reduction in inflammation, pain, or autoimmune-induced tissue damage, or prolonged survival of transplanted tissue or organs. Additionally, a therapeutically effective dose or amount may reduce the need for immunosuppressive or anti-inflammatory drugs.

In another aspect, dendritic cells comprising an inhibitor of miR-181 are used in the practice of the invention. Inhibitors of miR-181 can include, but are not limited to, antisense oligonucleotides, inhibitory RNA molecules, such as miRNAs, siRNAs, shRNAs, piRNAs, and snRNAs, ribozymes, and small molecule inhibitors. Various types of inhibitors for inhibiting nucleic acid function are well known in the art. See e.g., International patent application WO/2012/018881; U.S. patent application 2011/0251261; U.S. Pat. No. 6,713,457; Kole et al. (2012) Nat. Rev. Drug Discov. 11(2):125-40; Sanghvi (2011) Curr. Protoc. Nucleic Acid Chem. Chapter 4: Unit 4.1.1-22; herein incorporated by reference in their entireties.

Inhibitors can be single stranded or double stranded polynucleotides and may contain one or more chemical modifications, such as, but not limited to, locked nucleic acids, peptide nucleic acids, sugar modifications, such as 2'-O-alkyl (e.g., 2'-O-methyl, 2'-O-methoxyethyl), 2'-fluoro, and 4'-thio modifications, and backbone modifications, such as one or more phosphorothioate, morpholino, or phosphonocarboxylate linkages. In addition, inhibitory RNA molecules may have a "tail" covalently attached to their 3'- and/or 5'-end, which may be used to stabilize the RNA inhibitory molecule or enhance cellular uptake. Such tails include, but are not limited to, intercalating groups, various kinds of reporter groups, and lipophilic groups attached to the 3' or 5' ends of the RNA molecules. In certain embodiments, the RNA inhibitory molecule is conjugated to cholesterol or acridine. See, for example, the following for descriptions of syntheses of 3'-cholesterol or 3'-acridine modified oligonucleotides: Gamper, H. B., Reed, M. W., Cox, T., Virosco, J. S., Adams, A. D., Gall, A., Scholler, J. K., and Meyer, R. B. (1993) Facile Preparation and Exonuclease Stability of 3'-Modified Oligodeoxynucleotides. Nucleic Acids Res. 21:145-150; and Reed, M. W., Adams, A. D., Nelson, J. S., and Meyer, R. B., Jr. (1991) Acridine and Cholesterol-Derivatized Solid Supports for Improved Synthesis of 3'-Modified Oligonucleotides. Bioconjugate Chem. 2:217-225 (1993); herein incorporated by reference in their entireties. Additional lipophilic moieties that can be used, include, but are not limited to, oleyl, retinyl, and cholesteryl residues, cholic acid, adamantane acetic acid, 1-pyrene butyric acid, dihydrotestosterone, 1,3-Bis-O(hexadecyl) glycerol, geranyloxyhexyl group, hexadecylglycerol, borneol, menthol, 1,3-propanediol, heptadecyl group, palmitic acid, myristic acid, $O_3$-(oleoyl)lithocholic acid, $O_3$-(oleoyl) cholenic acid, dimethoxytrityl, or phenoxazine. Additional compounds, and methods of use, are set out in US Patent Publication Nos. 2010/0076056, 2009/0247608 and 2009/0131360; herein incorporated by reference in their entireties.

In one embodiment, inhibition of miR-181 function may be achieved by administering antisense oligonucleotides targeting miR-181. The antisense oligonucleotides may be ribonucleotides or deoxyribonucleotides. Preferably, the antisense oligonucleotides have at least one chemical modification. Antisense oligonucleotides may be comprised of one or more "locked nucleic acids". "Locked nucleic acids" (LNAs) are modified ribonucleotides that contain an extra bridge between the 2' and 4' carbons of the ribose sugar moiety resulting in a "locked" conformation that confers enhanced thermal stability to oligonucleotides containing the LNAs. Alternatively, the antisense oligonucleotides may comprise peptide nucleic acids (PNAs), which contain a peptide-based backbone rather than a sugar-phosphate backbone. The antisense oligonucleotides may contain one or more chemical modifications, including, but are not limited to, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages (see, for example, U.S. Pat. Nos. 6,693,187 and 7,067,641, which are herein incorporated by reference in their entireties). In some embodiments, suitable antisense oligonucleotides are 2'-O-methoxyethyl "gapmers" which contain 2'-O-methoxyethyl-modified ribonucleotides on both 5' and 3' ends with at least ten deoxyribonucleotides in the center. These "gapmers" are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the methods of the invention. Antisense oligonucleotides may comprise a sequence that is at least partially complementary to a miR-181 target sequence, e.g., at least about 75%, 80%, 85%, 90%, 91%, 92%, 93%, 94%, 95%, 96%, 97%, 98%, or 99% complementary to the miR-181 target sequence. In some embodiments, the antisense oligonucleotide may be substantially complementary to the miR-181 target sequence, that is at least about 95%, 96%, 97%, 98%, or 99% complementary to a target polynucleotide sequence. In one embodiment, the antisense oligonucleotide comprises a sequence that is 100% complementary to the miR-181 target sequence. In one embodiment, the antisense oligonucleotide targets a miR-181 comprising a sequence selected from the group consisting of SEQ ID NOS:1-6.

In another embodiment, the inhibitor of miR-181 is an inhibitory RNA molecule (e.g., a miRNA, a siRNA, shRNA, a piRNA, or a snRNA) having a single-stranded or double-stranded region that is at least partially complementary to the target sequence of miR-181, e.g., about 75%, 80%, 85%, 90%, 91%, 92%, 93%, 94%, 95%, 96%, 97%, 98%, or 99% complementary to the target sequence of miR-181. In some embodiments, the inhibitory RNA comprises a sequence that is substantially complementary to the target sequence of miR-181, e.g., about 95%, 96%, 97%, 98%, or 99% complementary to a target polynucleotide sequence. In other embodiments, the inhibitory RNA molecule may contain a region that has 100% complementarity to the target sequence. In one embodiment, the inhibitory molecule targets a miR-181 comprising a sequence selected from the group consisting of SEQ ID NOS:1-6. In certain embodiments, the inhibitory RNA molecule may be a double-stranded, small interfering RNA or a short hairpin RNA molecule (shRNA) comprising a stem-loop structure.

In certain embodiments, a modified dendritic cell comprises an "effective amount" of a miR-181 inhibitor (e.g., microRNA, siRNA, shRNA, piRNA, snRNA, antisense oligonucleotide, ribozyme, or small molecule inhibitor), that is, an amount sufficient to reduce miR-181 activity in a dendritic cell, for example, by interfering with transcription of miR-181, increasing degradation of the miR-181 transcript, or interfering with gene regulatory activity of miR-181. In some embodiments, a miR-181 inhibitor reduces the amount and/or activity of miR-181 in a dendritic cell by at least about 10% to about 100%, 20% to about 100%, 30% to about 100%, 40% to about 100%, 50% to about 100%, 60% to about 100%, 70% to about 100%, 10% to about 90%, 20% to about 85%, 40% to about 84%, 60% to about 90%, including any percent within these ranges, such as but not limited to 15%, 20%, 25%, 30%, 35%, 40%, 45%, 50%, 55%, 60%, 65%, 70%, 75%, 80%, 85%, 90%, 95%, 96%, 97%, 98%, and 99%. Preferably, the miR-181 inhibitor also enhances the immunogenic properties of a dendritic cell.

In one embodiment, the invention includes a method of modulating an immune response in a subject, the method comprising administering a therapeutically effective amount of a composition comprising immunogenic dendritic cells (e.g., dendritic cells transfected with an inhibitor of miR-181 or a recombinant polynucleotide encoding it) to the subject, wherein the composition comprising immunogenic dendritic cells is administered in an amount sufficient to enhance an immune response in a subject. A "therapeutically effective dose or amount" of a composition comprising immunogenic dendritic cells (e.g., dendritic cells transfected with an inhibitor of miR-181 or a recombinant polynucleotide encoding it) is intended an amount that, when administered as described herein, brings about a positive therapeutic response, such as improved recovery from cancer, an infection, or immunodeficiency. Improved recovery may include enhanced immunity or eradication of an infectious pathogen or cancerous cells. Additionally, a therapeutically effective dose or amount may have anti-tumor activity.

In certain embodiments, the miR-181 or a mimic or inhibitor thereof is expressed in vivo from a vector. A "vector" is a composition of matter which can be used to deliver a nucleic acid of interest to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. Examples of viral vectors include, but are not limited to, adenoviral vectors, adeno-associated virus vectors, retroviral vectors, lentiviral vectors, and the like. An expression construct can be replicated in a living cell, or it can be made synthetically. For purposes of this application, the terms "expression construct," "expression vector," and "vector," are used interchangeably to demonstrate the application of the invention in a general, illustrative sense, and are not intended to limit the invention.

In one embodiment, an expression vector for expressing miR-181 or a mimic or inhibitor thereof comprises a promoter "operably linked" to a polynucleotide encoding the miR-181 or a mimic or inhibitor thereof. The phrase "operably linked" or "under transcriptional control" as used herein means that the promoter is in the correct location and orientation in relation to a polynucleotide to control the initiation of transcription by RNA polymerase and expression of the polynucleotide.

In certain embodiments, the nucleic acid encoding a polynucleotide of interest is under transcriptional control of a promoter. A "promoter" refers to a DNA sequence recognized by the synthetic machinery of the cell, or introduced synthetic machinery, required to initiate the specific transcription of a gene. The term promoter will be used here to refer to a group of transcriptional control modules that are clustered around the initiation site for RNA polymerase I, II, or III. Typical promoters for mammalian cell expression include the SV40 early promoter, a CMV promoter such as the CMV immediate early promoter (see, U.S. Pat. Nos. 5,168,062 and 5,385,839, incorporated herein by reference in their entireties), the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. These and other promoters can be obtained from commercially available plasmids, using techniques well known in the art. See, e.g., Sambrook et al., supra. Enhancer elements may be used in association with the promoter to increase expression levels of the constructs. Examples include the SV40 early gene enhancer, as described in Dijkema et al., *EMBO J.* (1985) 4:761, the enhancer/promoter derived from the long terminal repeat (LTR) of the Rous Sarcoma Virus, as described in Gorman et al., *Proc. Natl. Acad. Sci. USA* (1982b) 79:6777 and elements derived from human CMV, as described in Boshart et al., *Cell* (1985) 41:521, such as elements included in the CMV intron A sequence.

Typically, transcription terminator/polyadenylation signals will also be present in the expression construct. Examples of such sequences include, but are not limited to, those derived from SV40, as described in Sambrook et al., supra, as well as a bovine growth hormone terminator sequence (see, e.g., U.S. Pat. No. 5,122,458). Additionally, 5'-UTR sequences can be placed adjacent to the coding sequence in order to enhance expression of the same. Such sequences include UTRs which include an Internal Ribosome Entry Site (IRES) present in the leader sequences of picornaviruses such as the encephalomyocarditis virus (EMCV) UTR (Jang et al. *J. Virol.* (1989) 63:1651-1660. Other picornavirus UTR sequences that will also find use in the present invention include the polio leader sequence and hepatitis A virus leader and the hepatitis C IRES.

In certain embodiments of the invention, the cells containing nucleic acid constructs of the present invention may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants, for example, genes that confer resistance to neomycin, puromycin, hygromycin, DHFR, GPT, zeocin and histidinol are useful selectable markers. Alternatively, enzymes such as herpes simplex virus thymidine kinase (tk) or chloramphenicol acetyltransferase (CAT) may be employed. Fluorescent markers (e.g., GFP, EGFP, Dronpa, mCherry, mOrange, mPlum, Venus, YPet, phycoerythrin), or immunologic markers can also be employed. The selectable marker employed is not believed to be important, so long as it is capable of being expressed simultaneously with the nucleic acid encoding a gene product. Further examples of selectable markers are well known to one of skill in the art.

There are a number of ways in which expression vectors may be introduced into dendritic cells. In certain embodiments of the invention, the expression construct comprises a virus or engineered construct derived from a viral genome. A number of viral based systems have been developed for gene transfer into mammalian cells. These include adenoviruses, retroviruses (γ-retroviruses and lentiviruses), poxviruses, adeno-associated viruses, baculoviruses, and herpes simplex viruses (see e.g., Warnock et al. (2011) Methods Mol. Biol. 737:1-25; Walther et al. (2000) Drugs 60(2):249-271; and Lundstrom (2003) Trends Biotechnol. 21(3):117-122; herein incorporated by reference in their entireties). The ability of certain viruses to enter cells via receptor-mediated endocytosis, to integrate into host cell genomes and express viral genes stably and efficiently have made them attractive candidates for the transfer of foreign genes into mammalian cells.

For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; Boris-Lawrie and Temin (1993) Cur. Opin. Genet. Develop. 3:102-109; and Ferry et al. (2011) Curr. Pharm. Des. 17(24):2516-2527). Lentiviruses are a class of retroviruses that are particularly useful for delivering polynucleotides to mammalian cells because they are able to infect both dividing and nondividing cells (see e.g., Lois et al (2002) Science 295:868-872; Durand et al. (2011) Viruses 3(2):132-159; herein incorporated by reference).

A number of adenovirus vectors have also been described. Unlike retroviruses which integrate into the host genome, adenoviruses persist extrachromosomally thus minimizing the risks associated with insertional mutagenesis (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476). Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., Molec. Cell Biol. (1988) 8:3988-3996; Vincent et al., Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Another vector system useful for delivering the polynucleotides of the present invention is the enterically administered recombinant poxvirus vaccines described by Small, Jr., P. A., et al. (U.S. Pat. No. 5,676,950, issued Oct. 14, 1997, herein incorporated by reference).

Additional viral vectors which will find use for delivering the nucleic acid molecules of interest include those derived from the pox family of viruses, including vaccinia virus and avian poxvirus. By way of example, vaccinia virus recombinants expressing a nucleic acid molecule of interest (e.g., miR-181 or a mimic or inhibitor thereof) can be constructed as follows. The DNA encoding the particular nucleic acid sequence is first inserted into an appropriate vector so that it is adjacent to a vaccinia promoter and flanking vaccinia DNA sequences, such as the sequence encoding thymidine kinase (TK). This vector is then used to transfect dendritic cells which are simultaneously infected with vaccinia. Homologous recombination serves to insert the vaccinia promoter plus the gene encoding the sequences of interest into the viral genome. The resulting TK-recombinant can be selected by culturing the dendritic cells in the presence of 5-bromodeoxyuridine and picking viral plaques resistant thereto.

Alternatively, avipoxviruses, such as the fowlpox and canarypox viruses, can also be used to deliver the nucleic acid molecules of interest. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with respect to the production of vaccinia viruses. See, e.g., WO 91/12882; WO 89/03429; and WO 92/03545.

Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for gene delivery.

Members of the Alphavirus genus, such as, but not limited to, vectors derived from the Sindbis virus (SIN), Semliki Forest virus (SFV), and Venezuelan Equine Encephalitis virus (VEE), will also find use as viral vectors for delivering the polynucleotides of the present invention. For a description of Sindbis-virus derived vectors useful for the practice of the instant methods, see, Dubensky et al. (1996) J. Virol. 70:508-519; and International Publication Nos. WO 95/07995, WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference. Particularly preferred are chimeric alphavirus vectors comprised of sequences derived from Sindbis virus and Venezuelan equine encephalitis virus. See, e.g., Perri et al. (2003) J. Virol. 77: 10394-10403 and International Publication Nos.

WO 02/099035, WO 02/080982, WO 01/81609, and WO 00/61772; herein incorporated by reference in their entireties.

A vaccinia based infection/transfection system can be conveniently used to provide for inducible, transient expression of the polynucleotides of interest (e.g., miR-181 or a mimic or inhibitor thereof) in a host dendritic cell. In this system, dendritic cells are first infected in vitro with a vaccinia virus recombinant that encodes the bacteriophage T7 RNA polymerase. This polymerase displays exquisite specificity in that it only transcribes templates bearing T7 promoters. Following infection, dendritic cells are transfected with the polynucleotide of interest, driven by a T7 promoter. The polymerase expressed in the cytoplasm from the vaccinia virus recombinant transcribes the transfected DNA into RNA. The method provides for high level, transient, cytoplasmic production of large quantities of RNA. See, e.g., Elroy-Stein and Moss, Proc. Natl. Acad. Sci. USA (1990) 87:6743-6747; Fuerst et al., Proc. Natl. Acad. Sci. USA (1986) 83:8122-8126.

As an alternative approach to infection with vaccinia or avipox virus recombinants, or to the delivery of nucleic acids using other viral vectors, an amplification system can be used that will lead to high level expression following introduction into host dendritic cells. Specifically, a T7 RNA polymerase promoter preceding the coding region for T7 RNA polymerase can be engineered. Translation of RNA derived from this template will generate T7 RNA polymerase which in turn will transcribe more templates. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, J. Mol. Biol. (1986) 189:113-130; Deng and Wolff, Gene (1994) 143:245-249; Gao et al., Biochem. Biophys. Res. Commun. (1994) 200:1201-1206; Gao and Huang, Nuc. Acids Res. (1993) 21:2867-2872; Chen et al., Nuc. Acids Res. (1994) 22:2114-2120; and U.S. Pat. No. 5,135,855.

In order to effect expression of sense or antisense gene constructs, the expression construct must be delivered into a dendritic cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include the use of calcium phosphate precipitation, DEAE-dextran, electroporation, direct microinjection, DNA-loaded liposomes, lipofectamine-DNA complexes, cell sonication, gene bombardment using high velocity microprojectiles, and receptor-mediated transfection (see, e.g., Graham and Van Der Eb (1973) Virology 52:456-467; Chen and Okayama (1987) Mol. Cell Biol. 7:2745-2752; Rippe et al. (1990) Mol. Cell Biol. 10:689-695; Gopal (1985) Mol. Cell Biol. 5:1188-1190; Tur-Kaspa et al. (1986) Mol. Cell. Biol. 6:716-718; Potter et al. (1984) Proc. Natl. Acad. Sci. USA 81:7161-7165); Harland and Weintraub (1985) J. Cell Biol. 101: 1094-1099); Nicolau and Sene (1982) Biochim. Biophys. Acta 721:185-190; Fraley et al. (1979) Proc. Natl. Acad. Sci. USA 76:3348-3352; Fechheimer et al. (1987) Proc Natl. Acad. Sci. USA 84:8463-8467; Yang et al. (1990) Proc. Natl. Acad. Sci. USA 87:9568-9572; Wu and Wu (1987) J. Biol. Chem. 262:4429-4432; Wu and Wu (1988) Biochemistry 27:887-892; herein incorporated by reference). Some of these techniques may be successfully adapted for in vivo or ex vivo use.

Once the expression construct has been delivered into the dendritic cell the nucleic acid encoding the gene of interest may be positioned and expressed at different sites. In certain embodiments, the nucleic acid encoding the gene may be stably integrated into the genome of the dendritic cell. This integration may be in the cognate location and orientation via homologous recombination (gene replacement) or it may be integrated in a random, non-specific location (gene augmentation). In yet further embodiments, the nucleic acid may be stably maintained in the dendritic cell as a separate, episomal segment of DNA. Such nucleic acid segments or "episomes" encode sequences sufficient to permit maintenance and replication independent of or in synchronization with the host cell cycle. How the expression construct is delivered to a dendritic cell and where in the dendritic cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (Proc. Natl. Acad. Sci. USA (1984) 81:7529-7533) successfully injected polyomavirus DNA in the form of calcium phosphate precipitates into liver and spleen of adult and newborn mice demonstrating active viral replication and acute infection. Benvenisty and Neshif (Proc. Natl. Acad. Sci. USA (1986) 83:9551-9555) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment, a naked DNA expression construct may be transferred into dendritic cells by particle bombardment. This method depends on the ability to accelerate DNA-coated microprojectiles to a high velocity allowing them to pierce cell membranes and enter cells without killing them (Klein et al. (1987) Nature 327:70-73). Several devices for accelerating small particles have been developed. One such device relies on a high voltage discharge to generate an electrical current, which in turn provides the motive force (Yang et al. (1990) Proc. Natl. Acad. Sci. USA 87:9568-9572). The microprojectiles may consist of biologically inert substances, such as tungsten or gold beads.

In a further embodiment, the expression construct may be delivered using liposomes. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat (1991) Liver Diseases, Targeted Diagnosis and Therapy Using Specific Receptors and Ligands, Wu et al. (Eds.), Marcel Dekker, N.Y., 87-104). Also contemplated is the use of lipofectamine-DNA complexes.

In certain embodiments of the invention, the liposome may be complexed with a hemagglutinating virus (HVJ). This has been shown to facilitate fusion with the cell membrane and promote cell entry of liposome-encapsulated DNA (Kaneda et al. (1989) Science 243:375-378). In other embodiments, the liposome may be complexed or employed in conjunction with nuclear non-histone chromosomal proteins (HMG-I) (Kato et al. (1991) J. Biol. Chem. 266(6): 3361-3364). In yet further embodiments, the liposome may be complexed or employed in conjunction with both HVJ and HMG-I. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid into dendritic cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu (1993) Adv. Drug Delivery Rev. 12:159-167).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) and transferrin (see, e.g., Wu and Wu (1987), supra; Wagner et al. (1990) Proc. Natl. Acad. Sci. USA 87(9):3410-3414). Recently, a synthetic neoglycoprotein, which recognizes the same receptor as ASOR, has been used as a gene delivery vehicle (Ferkol et al. (1993) FASEB J. 7:1081-1091; Perales et al. (1994) Proc. Natl. Acad. Sci. USA 91(9):4086-4090), and epidermal growth factor (EGF) has also been used to deliver genes to squamous carcinoma cells (Myers, EPO 0273085).

In other embodiments, the delivery vehicle may comprise a ligand and a liposome. For example, Nicolau et al. (Methods Enzymol. (1987) 149:157-176) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a dendritic cell by any number of receptor-ligand systems with or without liposomes. Also, antibodies to surface antigens on dendritic cells can similarly be used as targeting moieties.

In a particular example, an oligonucleotide may be administered in combination with a cationic lipid. Examples of cationic lipids include, but are not limited to, lipofectin, DOTMA, DOPE, and DOTAP. The publication of WO/0071096, which is specifically incorporated by reference, describes different formulations, such as a DOTAP: cholesterol or cholesterol derivative formulation that can effectively be used for gene therapy. Other disclosures also discuss different lipid or liposomal formulations including nanoparticles and methods of administration; these include, but are not limited to, U.S. Patent Publication 20030203865, 20020150626, 20030032615, and 20040048787, which are specifically incorporated by reference to the extent they disclose formulations and other related aspects of administration and delivery of nucleic acids. Methods used for forming particles are also disclosed in U.S. Pat. Nos. 5,844,107, 5,877,302, 6,008,336, 6,077,835, 5,972,901, 6,200,801, and 5,972,900, which are incorporated by reference for those aspects.

In certain embodiments, gene transfer may more easily be performed under ex vivo conditions. Ex vivo gene therapy refers to the isolation of dendritic cells from a subject, the delivery of a nucleic acid into the dendritic cells in vitro, and then the return of the modified dendritic cells back into the subject. This may involve the collection of a biological sample comprising dendritic cells from the subject, such as, but not limited to, blood, liver, skin, synovial tissue, interstitial tissues, nose, lungs, stomach, intestines, bone marrow, lymph nodes, thymus, spleen, or another hematopoietic or lymphoid organ. For example, blood can be obtained by venipuncture, and solid tissue samples can be obtained by surgical techniques according to methods well known in the art.

Usually, but not always, the subject who receives the dendritic cells (i.e., the recipient) is also the subject from whom the dendritic cells are harvested or obtained, which provides the advantage that the donated cells are autologous. However, dendritic cells can be obtained from another subject (i.e., donor), a culture of cells from a donor, or from established cell culture lines. Dendritic cells may be obtained from the same or a different species than the subject to be treated, but preferably are of the same species, and more preferably of the same immunological profile as the subject. Such cells can be obtained, for example, from a biological sample comprising dendritic cells from a close relative or matched donor, then transfected with nucleic acids (e.g., encoding miR-181 or a mimic or inhibitor thereof), and administered to a subject in need of treatment for an immune disease or condition.

In certain embodiments, the dendritic cells administered to a subject are autologous or allogeneic. The patients or subjects who donate or receive the dendritic cells are typically mammalian, and usually human. However, this need not always be the case, as veterinary applications are also contemplated.

Additionally, dendritic cells may be expanded in culture prior to administration to a subject. For a description of techniques for culturing dendritic cells, see, e.g., Human Cell Culture: Primary Hematopoietic Cells (Volume 4), pp. 171-191, Springer, 2002; Macrophages and Dendritic Cells: Methods and Protocols (Methods in Molecular Biology), N. E. Reiner ed., Humana Press, 2009; Dendritic Cells, $2^{nd}$ edition: Biology and Clinical Applications, M. T. Lotze and A. W. Thomson eds., Academic Press, $2^{nd}$ edition, 2001; Celluzzi et al. (2003) J. Hematother. Stem Cell Res. 12(5): 575-585; herein incorporated by reference in their entireties.

Alternatively, dendritic cells can be derived from monocytes collected from a subject. Differentiation of monocytes into dendritic cells can be accomplished, for example, by growing monocytes in culture in the presence of GM-CSF and IL-4, by exposure to serum proteins, such as for example fibronectin or vitronectin, or using transimmunization. See, e.g., Dauer et al. (2003) J. Immunol. 170(8):4069-4076; Caux et al. (1992) Nature 360(6401):258-261; Romani et al. (1994) J. Exp. Med. 180(1):83-93; Sallusto et al. (1994) J. Exp. Med. 179(4):1109-1118; and U.S. Pat. No. 8,313,945; herein incorporated by reference in their entireties.

Dendritic cells can be isolated from samples using any method known in the art, including, but not limited to, density gradient centrifugation (e.g., Ficoll Hypaque, percoll, iodoxanol and sodium metrizoate), immunoselection (positive selection or negative selection for surface markers)

with immunomagnetic beads or immunoaffinity columns, or fluorescence-activated cell sorting (FACS).

The miR-181 or mimic or inhibitor thereof may comprise a detectable label in order to determine cellular uptake efficiency, quantitate binding at target sites, or visualize localization. Detectable labels suitable for use in the present invention include any composition detectable by spectroscopic, photochemical, biochemical, immunochemical, electrical, optical, or chemical means. Useful labels in the present invention include biotin or other streptavidin-binding proteins for staining with labeled streptavidin conjugate, magnetic beads (e.g., Dynabeads), fluorescent dyes (e.g., phycoerythrin, YPet, fluorescein, texas red, rhodamine, green fluorescent protein, and the like, see, e.g., Molecular Probes, Eugene, Oreg., USA), radiolabels (e.g., $^{3}$H, $^{125}$I, $^{35}$S, $^{14}$C, or $^{32}$P), enzymes (e.g., horseradish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. In addition, magnetic resonance imaging (MRI) contrast agents (e.g., gadodiamide, gadobenic acid, gadopentetic acid, gadoteridol, gadofosveset, gadoversetamide, gadoxetic acid), and computed tomography (CT) contrast agents (e.g., Diatrizoic acid, Metrizoic acid, Iodamide, Iotalamic acid, Ioxitalamic acid, Ioglicic acid, Acetrizoic acid, Iocarmic acid, Methiodal, Diodone, Metrizamide, Iohexol, Ioxaglic acid, Iopamidol, Iopromide, Iotrolan, Ioversol, Iopentol, Iodixanol, Iomeprol, Iobitridol, Ioxilan, Iodoxamic acid, Iotroxic acid, Ioglycamic acid, Adipiodone, Iobenzamic acid, Iopanoic acid, Iocetamic acid, Sodium iopodate, Tyropanoic acid, Calcium iopodate) are useful as labels in medical imaging. Patents teaching the use of such labels include U.S. Pat. Nos. 3,817,837; 3,850,752; 3,939,350; 3,996,345; 4,277,437; 4,275,149; 4,366,241; 5,798,092; 5,695,739; 5,733,528; and 5,888,576.

B. Applications

The methods of the invention are useful for treating various immune conditions and disorders. For example, compositions comprising tolerogenic dendritic cells can be used in conjunction with tissue or organ transplantation for improving graft tolerance, prolonging survival of a transplanted tissue or organ, and treating graft-versus-host disease. In addition, tolerogenic dendritic cells can be used for decreasing inflammation such as caused by an autoimmune disease, allergic response, neurodegenerative disease, a cardiovascular disease, damaged tissue, or a wound. Inflammatory conditions and autoimmune diseases that may be treated with tolerogenic dendritic cells by the methods of the invention include, but are not limited to multiple sclerosis (MS), rheumatoid arthritis (RA), reactive arthritis, psoriasis, *pemphigus vulgaris*, Sjogren's disease, autoimmune thyroid disease (AITD), Hashimoto's thyroiditis, myasthenia gravis, diabetes mellitus type 1, stomatitis, lupus erythematosus, acute disseminated encephalomyelitis (ADEM), Addison's disease, agammaglobulinemia, alopecia areata, amyotrophic lateral sclerosis, ankylosing spondylitis, antiphospholipid syndrome, antisynthetase syndrome, atopic dermatitis, autoimmune aplastic anemia, autoimmune enteropathy, autoimmune hemolytic anemia, autoimmune hemolytic anemia, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticaria, autoimmune uveitis, Balo disease/Balo concentric sclerosis, Behçet's disease, Berger's disease, Bickerstaffs encephalitis, Blau syndrome, Bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease, Cushing's Syndrome, cutaneous leukocytoclastic angiitis, Dego's disease, Dercum's disease, dermatitis herpetiformis, dermatomyositis, diffuse cutaneous systemic sclerosis, Dressler's syndrome, eczema, endometriosis, enthesitis-related arthritis, eosinophilic fasciitis, eosinophilic gastroenteritis, eosinophilic pneumonia, epidermolysis bullosa acquisita, erythema nodosum, erythroblastosis fetalis, essential mixed cryoglobulinemia, Evan's syndrome, fibrodysplasia ossificans progressiva, fibrosing alveolitis (or idiopathic pulmonary fibrosis), gastritis, gastrointestinal pemphigoid, glomerulonephritis, Goodpasture's syndrome, Graves' disease, Guillain-Barré syndrome (GBS), Hashimoto's encephalopathy, Henoch-Schonlein purpura, gestational pemphigoid, hidradenitis suppurativa, Hughes-Stovin syndrome, hypogammaglobulinemia, idiopathic inflammatory demyelinating diseases, idiopathic pulmonary fibrosis, IgA nephropathy, inclusion body myositis, chronic inflammatory demyelinating polyneuropathy, interstitial cystitis, juvenile idiopathic arthritis, Kawasaki's disease, Lambert-Eaton myasthenic syndrome, leukocytoclastic vasculitis, lichen planus, lichen sclerosus, linear IgA disease (LAD), lupoid hepatitis, Majeed syndrome, Ménière's disease, microscopic polyangiitis, Miller-Fisher syndrome, mixed connective tissue disease, morphea, Mucha-Habermann disease, microscopic colitis, myositis, narcolepsy, neuromyelitis optica, neuromyotonia, occular cicatricial pemphigoid, opsoclonus myoclonus syndrome, Ord's thyroiditis, palindromic rheumatism, PANDAS, paraneoplastic cerebellar degeneration, paroxysmal nocturnal hemoglobinuria (PNH), Parry Romberg syndrome, Parsonage-Turner syndrome, Pars planitis, *pemphigus vulgaris*, pernicious anaemia, perivenous encephalomyelitis, POEMS syndrome, polyarteritis nodosa, polymyalgia rheumatica, polymyositis, primary biliary cirrhosis, primary sclerosing cholangitis, progressive inflammatory neuropathy, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatic fever, sarcoidosis, Schmidt syndrome, Schnitzler syndrome, scleritis, scleroderma, serum sickness, Sjögren's syndrome, spondyloarthropathy, Still's disease, Stiff person syndrome, Subacute bacterial endocarditis (SBE), Susac's syndrome, Sweet's syndrome, Sydenham chorea, sympathetic ophthalmia, Takayasu's arteritis, temporal arteritis, thrombocytopenia, Tolosa-Hunt syndrome, transverse myelitis, undifferentiated connective tissue disease, undifferentiated spondyloarthropathy, urticarial vasculitis, vasculitis, vitiligo, Wegener's granulomatosis, autoimmune cardiomyopathy, ischemic heart disease, atherosclerosis, cancer, fibrosis, inflammatory bowel disease, inflammatory myopathy, giant cell arteritis (GCA), asthma, allergy, Parkinson's disease, schizophrenia, and Alzheimer's disease.

In contrast, compositions comprising immunogenic dendritic cells can be used, for example, for treating infectious diseases, such as caused by a virus or cellular pathogen, increasing an immune response to a cancerous cell or tumor in an individual, or enhancing an immune response in an individual who is immunodeficient or immunocompromised. In some embodiments, immunogenic dendritic cells can be used to enhance an immune response for treating: (a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia), a picornavirus (e.g., rhinovirus or enterovirus), an orthomyxovirus (e.g., influenza virus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as human immunodeficiency virus (HIV)); (b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* and *Bordetella;* (c) other infectious diseases, such as, but not limited to *Chlamydia* infection, fungal diseases including but not limited to candidiasis, aspergillosis, blastomycosis, histoplasmosis, cryptococcal meningitis, and parasitic diseases including but not limited to malaria, *Pneumocystis carinii* pneumonia, leishmaniasis, cryptosporidiosis, toxoplasmosis, and trypanosome infection; (d) cancer, including squamous cell carcinoma, adenocarcinoma, adenosquamous carcinoma, anaplastic carcinoma, large cell carcinoma, or small cell carcinoma, including cancer in various tissues and organs, such as, but not limited to, breast cancer, prostate cancer, lung cancer, ovarian cancer, testicular cancer, colon cancer, pancreatic cancer, gastric cancer, hepatic cancer, leukemia, lymphoma, adrenal cancer, thyroid cancer, pituitary cancer, renal cancer, brain cancer, skin cancer, head cancer, neck cancer, oral cavity cancer, tongue cancer, and throat cancer; and (e) immunodeficiency, including primary and secondary immunodeficiencies, such as, but not limited to, immunodeficiency caused by acquired immune deficiency syndrome (AIDS), multiple myeloma, chronic lymphoid leukemia, lymphoma, chronic granulomatous disease, severe combined immunodeficiency (SCID), X-linked agammaglobulinemia, thymoma with immunodeficiency, common variable immunodeficiency (CVID), Wiskott-Aldrich syndrome, hepatic venoocclusive disease with immunodeficiency (VODI), sickle-cell anemia, bone marrow and other transplantation, splenectomy, cancer chemotherapy, disease-modifying antirheumatic drugs, glucocorticoid therapy, immunosuppressive drugs, and environmental exposure to toxins.

In addition, compositions comprising immunogenic dendritic cells may be administered in combination with a vaccine to augment the immune response to a cellular pathogen or cancerous cells. Compositions comprising immunogenic dendritic cells may also be used to enhance the immune response to antibiotic-resistant bacteria and for treating sepsis or food poisoning.

Treatment of primates, more particularly humans is of interest, but other mammals may also benefit from treatment, particularly domestic animals such as equine, bovine, ovine, feline, canine, murine, lagomorpha, and the like.

C. Pharmaceutical Compositions

The present invention also encompasses pharmaceutical compositions comprising modified dendritic cells (e.g., transfected with a miR-181 or a mimic or inhibitor thereof) and a pharmaceutically acceptable carrier. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

One will generally desire to employ appropriate salts and buffers to render delivery vehicles stable for the dendritic cells that are introduced into a patient. Aqueous compositions of the present invention comprise an effective amount of the delivery vehicle, dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antimicrobial agents, isotonic and absorption delaying agents, and the like acceptable for use in formulating pharmaceuticals, such as pharmaceuticals suitable for administration to humans. The use of such media and agents for pharmaceutically active substances is well known in the art. Except insofar as any conventional media or agent is incompatible with the modified dendritic cells of the present invention, its use in therapeutic compositions is contemplated. Supplementary active ingredients also can be incorporated into the compositions, provided they do not inactivate the miR-181 or mimic or inhibitor thereof in the transfected dendritic cells and are not harmful to the dendritic cells.

In certain embodiments, one or more additional factors, such as nutrients, cytokines, growth factors, antimicrobial agents, or anti-oxidants may be added to improve cell function or viability. The composition may also further comprise a pharmaceutically acceptable carrier.

Exemplary cytokines include, but are not limited to, granulocyte-macrophage colony-stimulating factor (GM-CSF), IL-4, IL-12, IL-2, IL-6, IL-1β, IL-10, IL-23, Flt3 ligand, IFN-α, IFN-β, IFN-γ, and TNF-α.

Exemplary growth factors include, but are not limited to, hepatocyte growth factor (HGF), transforming growth factor beta (TGF-β), and vascular endothelial growth factor (VEGF).

One or more pharmaceutically acceptable excipients may also be included. Exemplary excipients include, without limitation, carbohydrates, inorganic salts, antimicrobial agents, antioxidants, surfactants, buffers, acids, bases, and combinations thereof.

For example, an antimicrobial agent for preventing or deterring microbial growth may be included. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof. Antibmicrobial agents also include antibiotics that can also be used to prevent bacterial infection. Exemplary antibiotics include amoxicillin, penicillin, sulfa drugs, cephalosporins, erythromycin, streptomycin, gentamicin, tetracycline, chlarithromycin, ciproflozacin, azithromycin, and the like. Also included are antifungal agents such as myconazole and terconazole.

Various antioxidants can also be included, such as molecules having thiol groups such as reduced glutathione (GSH) or its precursors, glutathione or glutathione analogs, glutathione monoester, and N-acetylcysteine. Other suitable anti-oxidants include superoxide dismutase, catalase, vitamin E, Trolox, lipoic acid, lazaroids, butylated hvdroxyanisole (BHA), vitamin K, and the like.

Excipients suitable for injectable compositions include water, alcohols, polyols, glycerin, vegetable oils, phospholipids, and surfactants. A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like. The excipient can also include an inorganic salt or buffer such as citric acid, sodium chloride, potassium chloride, sodium sulfate, potassium nitrate, sodium phosphate monobasic, sodium phosphate dibasic, and combinations thereof.

Acids or bases can also be present as an excipient. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects. Generally, however, the excipient(s) will be present in the composition in an amount of about 1% to about 99% by weight, preferably from about 5% to about 98% by weight, more preferably from about 15 to about 95% by weight of the excipient, with concentrations less than 30% by weight most preferred. These foregoing pharmaceutical excipients along with other excipients are described in "Remington: The Science & Practice of Pharmacy", 19th ed., Williams & Williams, (1995), the "Physician's Desk Reference", 52nd ed., Medical Economics, Montvale, N.J. (1998), and Kibbe, A. H., Handbook of Pharmaceutical Excipients, 3rd Edition, American Pharmaceutical Association, Washington, D.C., 2000.

Compositions for use in the invention will comprise a therapeutically effective amount of the modified dendritic cells (e.g., transfected with a miR-181 or a mimic or inhibitor thereof). For example, a "therapeutically effective dose or amount" of a composition comprising tolerogenic dendritic cells (e.g., dendritic cells transfected with a miR-181 or miR-181 mimic) is an amount that, when administered as described herein, brings about a positive therapeutic response, such as improved recovery from an inflammatory condition, an allergy, or an autoimmune disorder, or better graft tolerance. Improved recovery may include a reduction in inflammation, pain, or autoimmune-induced tissue damage, or prolonged survival of transplanted tissue or organs. Additionally, a therapeutically effective dose or amount may reduce the need for immunosuppressive or anti-inflammatory drugs. By "therapeutically effective dose or amount" of a composition comprising immunogenic dendritic cells (e.g., dendritic cells transfected with an inhibitor of miR-181) is intended an amount that, when administered as described herein, brings about a positive therapeutic response, such as improved recovery from cancer, an infection, or immunodeficiency. Improved recovery may include enhanced immunity or eradication of an infectious pathogen. Additionally, a therapeutically effective dose or amount may have anti-tumor activity. An effective amount of modified dendritic cells (e.g., transfected with a miR-181 or a mimic or inhibitor thereof) can be administered in one or more administrations, applications or dosages.

The pharmaceutical preparation can be in the form of a suspension immediately prior to administration or other forms suitable for injectable use or catheter delivery. Generally, preparations are sterile and fluid to the extent that compositions can be easily injected. Preparations should be stable under the conditions of manufacture and storage and should be preserved against the contaminating action of microorganisms, such as bacteria and fungi. Isotonic agents may be included, for example, sugars or sodium chloride to stabilize cells.

The pharmaceutical preparations herein can also be housed in a syringe, an implantation device, or the like, depending upon the intended mode of delivery and use. Preferably, the compositions comprising dendritic cells, prepared as described herein, are in unit dosage form, meaning an amount of a composition appropriate for a single dose, in a premeasured or pre-packaged form.

The compositions herein may optionally include one or more additional agents, such as other drugs for treating immune diseases and conditions, or other medications used to treat a subject for a condition or disease. For example, compositions comprising tolerogenic dendritic cells (e.g., comprising a miR-181 or miR-181 mimic) may also contain one or more other drugs for treating transplantation, inflammation, an autoimmune disease, or allergy, such as, but not limited to, immunosuppressive agents, such as steroidal agents (e.g., prednisone) or non-steroidal agents (e.g., sirolimus (Rapamune, Wyeth-Ayerst Canada), tacrolimus (Prograf, Fujisawa Canada), anti-IL2R daclizumab (Zenapax, Roche Canada), 15-deoxyspergualin, cyclosporin, methotrexate, rapamycin, Rapamune (sirolimus/rapamycin), FK506, and Lisofylline (LSF); and anti-inflammatory/analgesic agents, including, but not limited to, non-steroidal anti-inflammatory drugs (NSAIDs), such as aspirin, ibuprofen, and naproxen, paracetamol, acetaminophen, COX-2 inhibitors, such as rofecoxib, celecoxib, and etoricoxib; opioids, such as morphine, codeine, oxycodone, hydrocodone, dihydromorphine, pethidine; and immune selective anti-inflammatory derivatives (ImSAIDs). Compositions comprising immunogenic dendritic cells (e.g., comprising a miR-181 inhibitor) may also contain one or more other drugs for treating cancer, an infection, or immunodeficiency, such as, but not limited to, chemotherapeutic agents, such as, but not limited to, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, leukeran, leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon; antimicrobial agents, including antiseptics, antibiotics, antifungal agents, antiviral agents, antiparasitic agents; and vaccines. Alternatively, such agents may be contained in a separate composition from the composition comprising the dendritic cells and co-administered concurrently, before, or after the composition comprising the dendritic cells.

D. Administration

At least one therapeutically effective cycle of treatment with modified dendritic cells (e.g., transfected with a miR-181 or a mimic or inhibitor thereof) will be administered to a subject for treatment of an immune disease or condition. By "therapeutically effective dose or amount" of a composition comprising tolerogenic dendritic cells (e.g., dendritic cells transfected with a miR-181 or miR-181 mimic) is intended an amount that, when administered as described herein, brings about a positive therapeutic response, such as improved recovery from an inflammatory condition, an allergy, or an autoimmune disorder, or better graft tolerance. Improved recovery may include a reduction in inflammation, pain, or autoimmune-induced tissue damage, or prolonged survival of transplanted tissue or organs. Additionally, a therapeutically effective dose or amount may reduce the need for immunosuppressive or anti-inflammatory drugs. By "therapeutically effective dose or amount" of a composition comprising immunogenic dendritic cells (e.g., dendritic cells transfected with an inhibitor of miR-181) is intended an amount that, when administered as described herein, brings about a positive therapeutic response, such as improved recovery from cancer, an infection, or immunodeficiency. Improved recovery may include enhanced immunity or eradication of an infectious pathogen. Additionally, a therapeutically effective dose or amount may have antitumor activity.

In certain embodiments, multiple therapeutically effective doses of compositions comprising modified dendritic cells and/or one or more other therapeutic agents, such as other drugs for treating immune diseases or conditions, or other medications will be administered. The compositions of the present invention are typically, although not necessarily, administered via injection (subcutaneously, intravenously, intra-arterially, or intramuscularly), by infusion, or locally. Additional modes of administration are also contemplated, such as intraperitoneal, intrathecal, intratumor, intralymphatic, intravascular, intralesion, transdermal, and so forth. In some embodiments, the pharmaceutical composition comprising modified dendritic cells (e.g., transfected with a miR-181 or a mimic or inhibitor thereof) is administered locally, for example, to the site of a tissue or organ transplant, or an infected, cancerous, or inflamed region needing treatment. The pharmaceutical compositions comprising dendritic cells and other agents may be administered using the same or different routes of administration in accordance with any medically acceptable method known in the art.

In another embodiment, the pharmaceutical compositions comprising modified dendritic cells (e.g., transfected with a miR-181 or a mimic or inhibitor thereof) are administered prophylactically, e.g., to prevent transplant rejection, inflammation, infection, or tumor growth. Such prophylactic uses will be of particular value for subjects with a disease or who have a genetic predisposition to developing an immune disease or condition, such as an autoimmune disease, infection (e.g., chronic granulomatous disease, osteopetrosis), immunodeficiency, inflammation, or cancer. For example, tolerogenic dendritic cells may be administered prior to transplant to prolong graft survival or to a patient with an autoimmune disease to prevent a disease flare. In another example, immunogenic dendritic cells may be administered to a patient who has had cancer previously and may be susceptible to relapse in order to prevent recurrence or to a person who is at high risk of developing cancer due to a genetic predisposition or environmental exposure to a carcinogen.

In another embodiment of the invention, the pharmaceutical compositions comprising modified dendritic cells and/or other agents are in a sustained-release formulation, or a formulation that is administered using a sustained-release device. Such devices are well known in the art, and include, for example, miniature implantable pumps that can provide for delivery over time in a continuous, steady-state fashion at a variety of doses to achieve a sustained-release effect with a non-sustained-release pharmaceutical composition.

Those of ordinary skill in the art will appreciate which conditions compositions comprising modified dendritic cells can effectively treat. The actual dose to be administered will vary depending upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case.

Compositions comprising modified dendritic cells, prepared as described herein (again, preferably provided as part of a pharmaceutical preparation), can be administered alone or in combination with one or more other therapeutic agents for treating an immune disease or condition, including other drugs for treating transplantation, inflammation, an autoimmune disease, or allergy, such as, but not limited to, immunosuppressive agents, such as steroidal agents (e.g., prednisone) or non-steroidal agents (e.g., sirolimus (Rapamune, Wyeth-Ayerst Canada), tacrolimus (Prograf, Fujisawa Canada), anti-IL2R daclizumab (Zenapax, Roche Canada), 15-deoxyspergualin, cyclosporin, methotrexate, rapamycin, Rapamune (sirolimus/rapamycin), FK506, and Lisofylline (LSF); and anti-inflammatory/analgesic agents, including, but not limited to, non-steroidal anti-inflammatory drugs (NSAIDs), such as aspirin, ibuprofen, and naproxen, paracetamol, acetaminophen, COX-2 inhibitors, such as rofecoxib, celecoxib, and etoricoxib; opioids, such as morphine, codeine, oxycodone, hydrocodone, dihydromorphine, pethidine; and immune selective anti-inflammatory derivatives (ImSAIDs); or other drugs for treating cancer, an infection, or immunodeficiency, such as, but not limited to, chemotherapeutic agents, such as, but not limited to, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, leukeran, leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon; antimicrobial agents, including antiseptics, antibiotics, antifungal agents, antiviral agents, antiparasitic agents; and vaccines; or other medications used to treat a particular condition or disease according to a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Preferred compositions are those requiring dosing no more than once a day.

Compositions comprising modified dendritic cells can be administered prior to, concurrent with, or subsequent to other agents. If provided at the same time as other agents, the modified dendritic cells can be provided in the same or in a different composition. Thus, modified dendritic cells and one or more other agents can be presented to the individual by way of concurrent therapy. By "concurrent therapy" is intended administration to a subject such that the therapeutic effect of the combination of the substances is caused in the subject undergoing therapy. For example, concurrent therapy may be achieved by administering a dose of a pharmaceutical composition comprising dendritic cells and a dose of a pharmaceutical composition comprising at least one other agent, such as a drug for treating an immune disease or condition, which in combination comprise a therapeutically effective dose, according to a particular dosing regimen. Similarly, the modified dendritic cells and one or more other therapeutic agents can be administered in at least one therapeutic dose. Administration of the separate pharmaceutical compositions can be performed simultaneously or at different times (i.e., sequentially, in either order, on the same day, or on different days), as long as the therapeutic effect of the combination of these substances is caused in the subject undergoing therapy.

E. Kits

Any of the compositions described herein may be included in a kit. For example dendritic cells (e.g., either already transfected with a miR-181 or miR-181 mimic or inhibitor or separate) may be included in a kit. The kit may also include polynucleotides for transfecting dendritic cells (e.g., a miR-181, miR-181 mimic, or miR-181 inhibitor, or recombinant polynucleotides encoding them) and one or more transfection reagents to facilitate delivery of polynucleotides to the dendritic cells. Such kits may also include components that preserve the polynucleotides or that protect against their degradation. Such components may be RNAse-free or protect against RNAses. The kit may also comprise agents for maintaining or culturing dendritic cells, such as, media, and optionally one or more other factors, such as cytokines, growth factors, antibiotics, and the like.

Such kits generally will comprise, in suitable means, distinct containers for each individual reagent or solution. The kit may comprise one or more containers holding the dendritic cells and/or polynucleotides (e.g., a miR-181, miR-181 mimic, or miR-181 inhibitor, or recombinant polynucleotides encoding them) and other agents. Suitable containers for the compositions include, for example, bottles, vials, syringes, and test tubes. Containers can be formed from a variety of materials, including glass or plastic. A container may have a sterile access port (for example, the container may be a vial having a stopper pierceable by a hypodermic injection needle).

The kit can further comprise a container comprising a pharmaceutically-acceptable buffer, such as phosphate-buffered saline, Ringer's solution, or dextrose solution. It can also contain other materials useful to the end-user, including other pharmaceutically acceptable formulating solutions such as buffers, diluents, filters, needles, and syringes or other delivery devices. The delivery device may be pre-filled with the compositions.

The kit can also comprise a package insert containing written instructions for methods of treating immune diseases and conditions with modified dendritic cells, as described herein. The package insert can be an unapproved draft package insert or can be a package insert approved by the Food and Drug Administration (FDA) or other regulatory body.

In one embodiment, the kit comprises tolerogenic dendritic cells, as described herein, or reagents (e.g., a miR-181 or mimic, dendritic cells, and transfection agents) for preparing such cells. The kit may also comprise means for delivering the composition to a subject and instructions for treating immune diseases and conditions benefitting from increased immunological tolerance, such as an inflammatory condition, an allergy, an autoimmune disorder, or organ or tissue transplantation.

In another embodiment, the kit comprises immunogenic dendritic cells, as described herein, or reagents (e.g., a miR-181 inhibitor, dendritic cells, and transfection agents) for preparing such cells. The kit may also comprise means for delivering the composition to a subject and instructions for treating immune diseases and conditions benefitting from an increased immunological response, such as cancer, an infection, or immunodeficiency.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

Role of MicroRNA-181a in Tolerogenic Properties of Plasmacytoid Dendritic Cells

Introduction

Liver allografts are well tolerated and other solid organ allografts show improved graft outcomes when transplanted concurrently with livers. However, the mechanisms underlying "hepatic tolerance" have yet to be elucidated. Previous studies have shown that hepatic dendritic cells (HDC) have diminished antigen presenting and immune stimulatory function compared with dendritic cells in lymphoid tissue (Abe et al. (2001) J. Hepatol. 34:61-67; Lau et al. (2006) J. Leukoc. Biol. 79:941-953). Recent studies have implicated increased frequency of plasmacytoid dendritic cells (pDC) to myeloid dendritic cells (mDC) in the liver in the underlying mechanism leading to hepatic tolerance (Pillarisetty et al. (2004) J. Immunol. 172:1009-1017; Gupta et al. (2009) Transplantation 88:589-594). It has been hypothesized that immature plasmacytoid dendritic cells (pDC) are inherently tolerogenic (Gupta et al. (2010) Transplantation 89(1):55-60).

We postulated that miRNA expression profiles would reveal differences between tolerogenic hepatic dendritic cells and other dendritic cells. Identifying specific miRNAs that are differentially expressed in tolerogenic dendritic cells could lead to the development of therapeutic methods to induce tolerogenic properties similar to those expressed by hepatic pDC in other dendritic cells that are not normally tolerogenic. Here we investigate the role of miR-181a in controlling the tolerogenic properties of dendritic cells.

Results

Comparison of Dendritic Cells from Liver and Spleen

Figure 5:
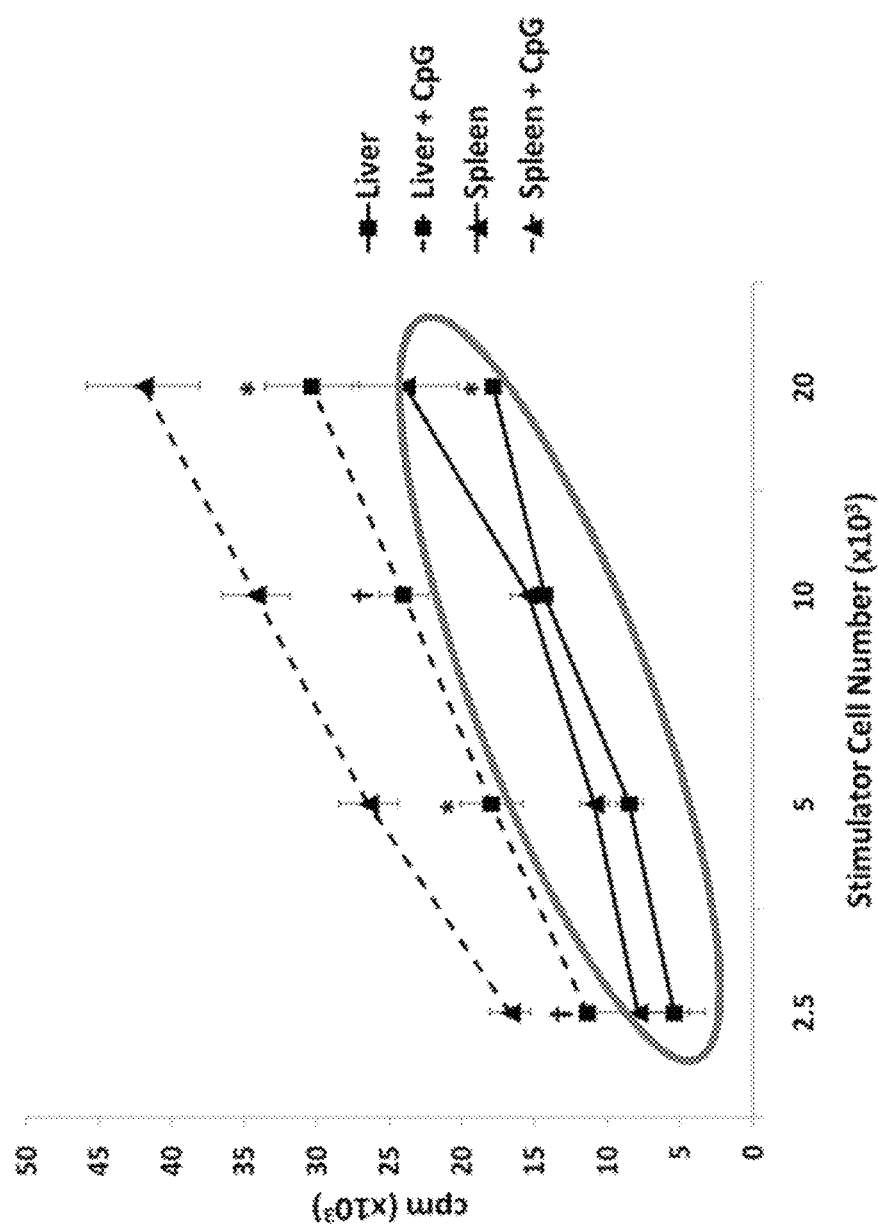
FIG. 5 shows T cell proliferative responses induced by hepatic or splenic DC with or without CpG stimulation in vivo.
Figure 6:
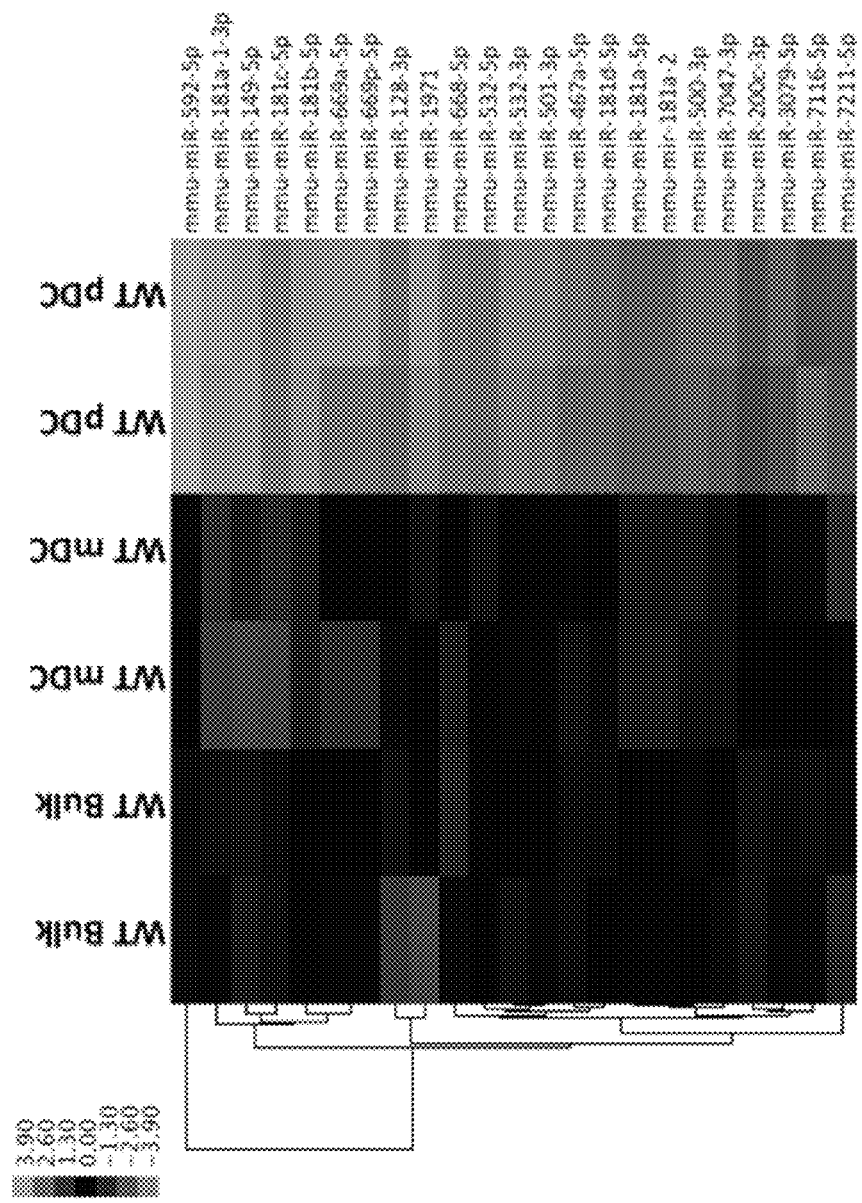
FIG. 6 shows a heatmap comparing microRNA expression in pDC with bulk dendritic cells and mDC.

Hepatic dendritic cells (HDC) have lower levels of MHC Class II and CD86 compared to spleen dendritic cells (SDC) as shown in Table 1. Consistent with the corresponding phenotypic data (Table 1), HDC were less efficient inducers of naive allogeneic T cell proliferation than control SDC at higher stimulator numbers (FIG. 5). Moreover, HDC from toll-like receptor (TLR; conserved pattern recognition molecules, which recognize bacterial and viral ligands) 9 ligand CpG-B-stimulated mice were poorer stimulators than their splenic counterparts (FIG. 5). These data show that HDC are inherently more immature and poorer allostimulators, even when stimulated, and thus may be more likely to contribute to alloAg tolerance.

TABLE 1

Freshly isolated hepatic pDC have lower surface expression of MHC class II and the classic costimulatory molecule CD86 compared to splenic pDC with or without CpG stimulation.

| pDC | MHCII | | CD86 | |
| --- | --- | --- | --- | --- |
| | % | MFI | % | MFI |
| Liver | 59.40 | 54.82 | 4.34 | 8.42 |
| Spleen | 88.54 | 22.55 | 32.6 | 8.25 |
| Liver + CpG | 28.82 | 28.70 | 13.77 | 10.84 |
| Spleen + CpG | 94.06 | 64.41 | 72.78 | 17.18 |

Wild-Type Hepatic Plasmacytoid Dendritic Cells Prolong Graft Survival

Figure 2A:
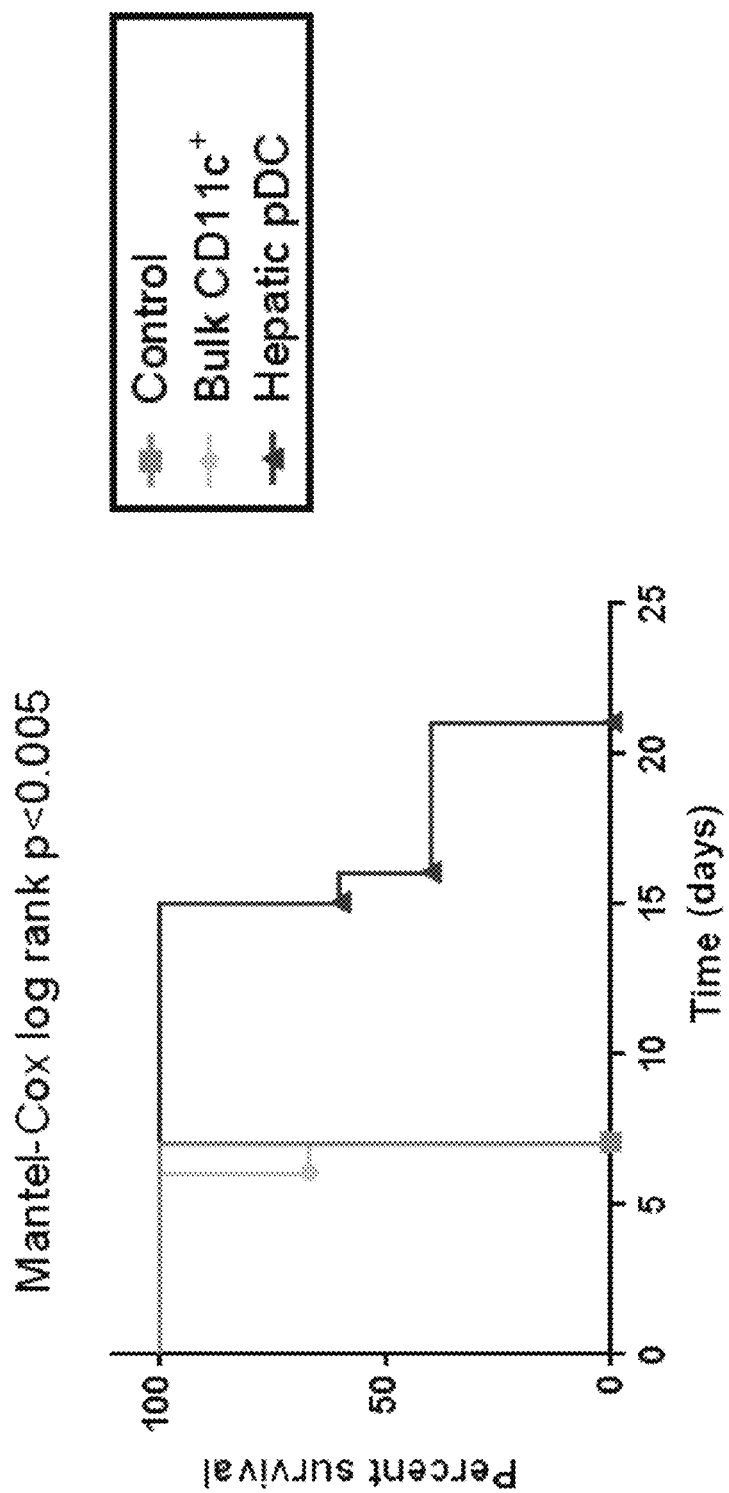
FIGS. 2A and 2B show that wild-type hepatic plasmacytoid dendritic cells (pDC) significantly prolong graft survival (FIG. 2A) and have significantly elevated levels of miR-181a (FIG. 2B) compared to myeloid DC. Immature pDC (CD11c$^{int}$PDCA-1+CD11b−) or myeloid DC (CD11c+ CD11b+PDCA−) from livers of wild type (WT) C57BL/6J mice were flow-sorted to >92% purity.
Figure 2B:
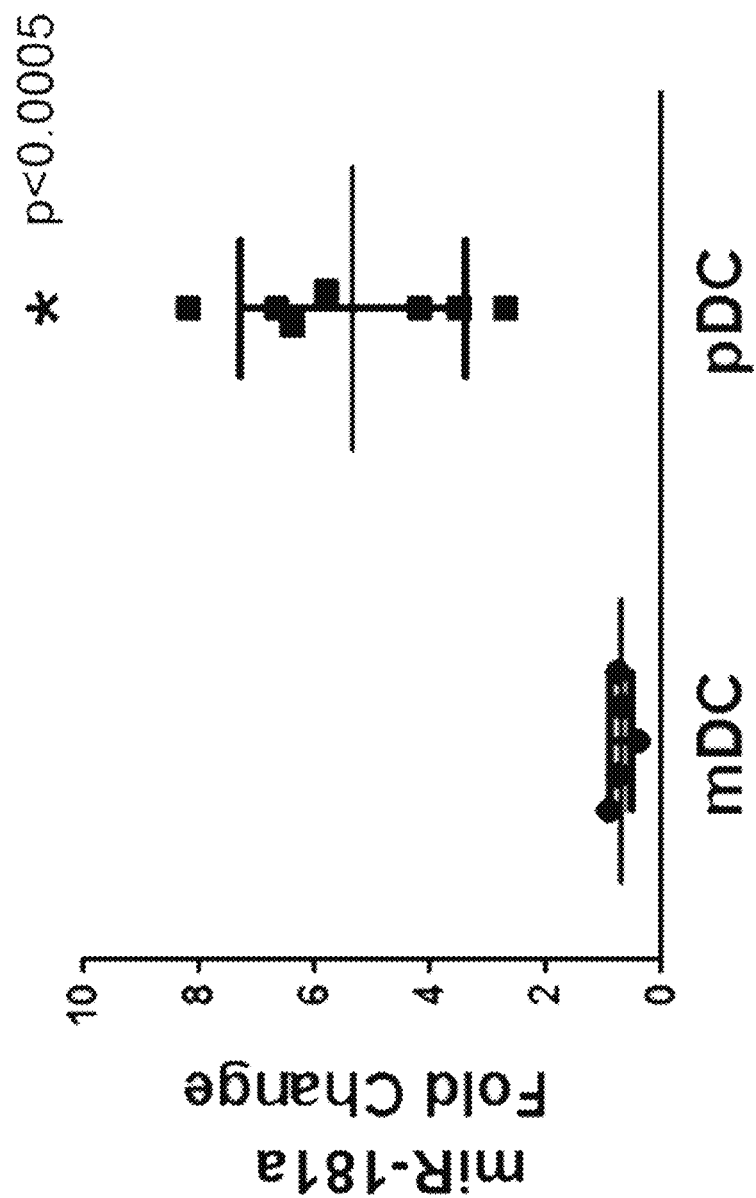

Immature pDC (CD11c$^{int}$ PDCA-1$^+$CD11b$^-$) or myeloid dendritic cells (mDC) (CD11c$^+$CD11b$^+$PDCA$^-$) from livers of wild type (WT) C57BL/6J mice were flow-sorted to greater than 92% purity. $5 \times 10^5$-$2 \times 10^6$ DC were injected intravenously into recipient BALB/cJ mice seven days prior to heterotopic cardiac allograft transplant using WT C57BL/6J donor hearts. P-values were determined using the Mantel-Cox log rank test. Quantitative polymerase chain reaction was performed for miR-181a. Results were from 5-7 samples with p-values determined using the Student's unpaired t-test. The results show that wild-type hepatic pDC significantly prolonged graft survival and had significantly elevated levels of miR-181a compared to mDC (FIG. 2).

Figure 4:
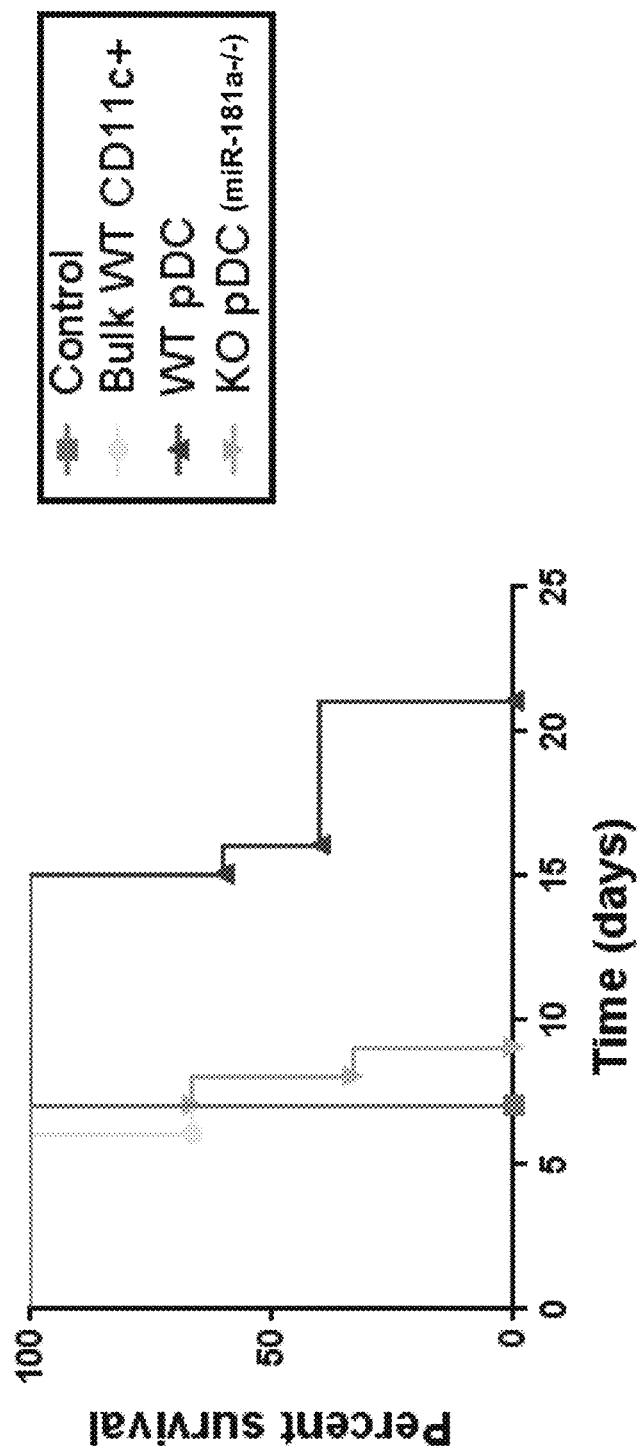
FIG. 4 shows that miR-181a is critical to the tolerogenic properties of hepatic plasmacytoid DC in prolonging cardiac allograft survival with lack of miR-181a in these cells abrogating their tolerogenic capacity. Immature pDC (CD11$^{int}$PDCA-1+CD11b-) or bulk CD11+ DC from livers of wild type (WT) or miR-181a$^{-/-}$ (KO) C57BL/6J mice were flow-sorted to greater than 92% purity. DC were injected intravenously into recipient BALB/cJ mice seven days prior to transplant and heterotopic cardiac allograft transplant using WT C57BL/6J donor hearts was performed on day 0. A Kaplan-Meier survival curve of cardiac transplant allograft survival is shown with three mice transplanted per group. Untreated control mice were used as control graft recipients. P-values were determined using the Mantel-Cox log rank test (*p<0.005).

Effect of miR-181a on Tolerogenic Properties of Hepatic Plasmacytoid DC in Prolonging Cardiac Allograft Survival Immature pDC (CD11$^{int}$PDCA-1+CD11b−) or bulk CD11c+ DC from livers of wild type (WT) or miR-181a$^{-/-}$ (KO) C57BL/6J mice were flow-sorted to greater than 92% purity. The DC were injected intravenously into recipient BALB/cJ mice seven days prior to transplant, and heterotopic cardiac allograft transplant using WT C57BL/6J donor hearts was performed on day 0. FIG. 4 shows a Kaplan-Meier survival curve of cardiac transplant allograft survival with three mice transplanted per group. Untreated control mice were used as control graft recipients. P-values were determined using the Mantel-Cox log rank test (*p<0.005). The results show that miR-181a is critical to the tolerogenic properties of hepatic plasmacytoid DC in prolonging cardiac allograft survival. The lack of miR-181a in dendritic cells from miR-181a$^{-/-}$ (KO) C57BL/6J mice abrogated their tolerogenic capacity.

Expression of Costimulatory Ligands CD40, CD80, and CD86

Figure 3A:
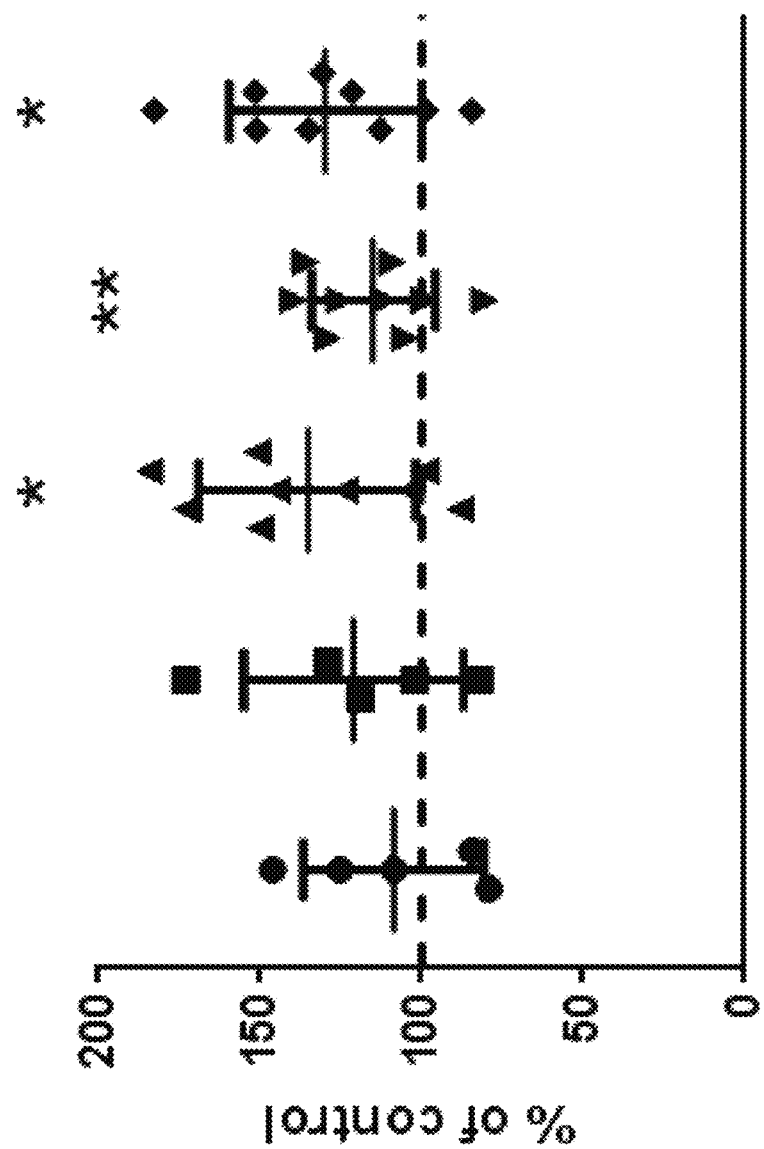
FIGS. 3A and 3B show that classic costimulatory molecule CD86 and major histocompatibility complex (MHC) II is more highly expressed on hepatic pDC from miR-181a$^{-/-}$ mice in comparison to WT when freshly isolated (FIG. 3A), but this difference is negated when cells are stimulated via toll-like receptor (TLR)9 (FIG. 3B). The pDC from livers of WT or miR-181a$^{-/-}$ (KO) C57BL/6J mice were examined by flow cytometry for the expression of classic costimulatory ligands CD40, CD80, and CD86; coinhibitory ligand programmed death ligand-1 (PD-L1); and MHCII. Geomeans measured on KO were expressed as a percentage compared to WT geomean.
Figure 3B:
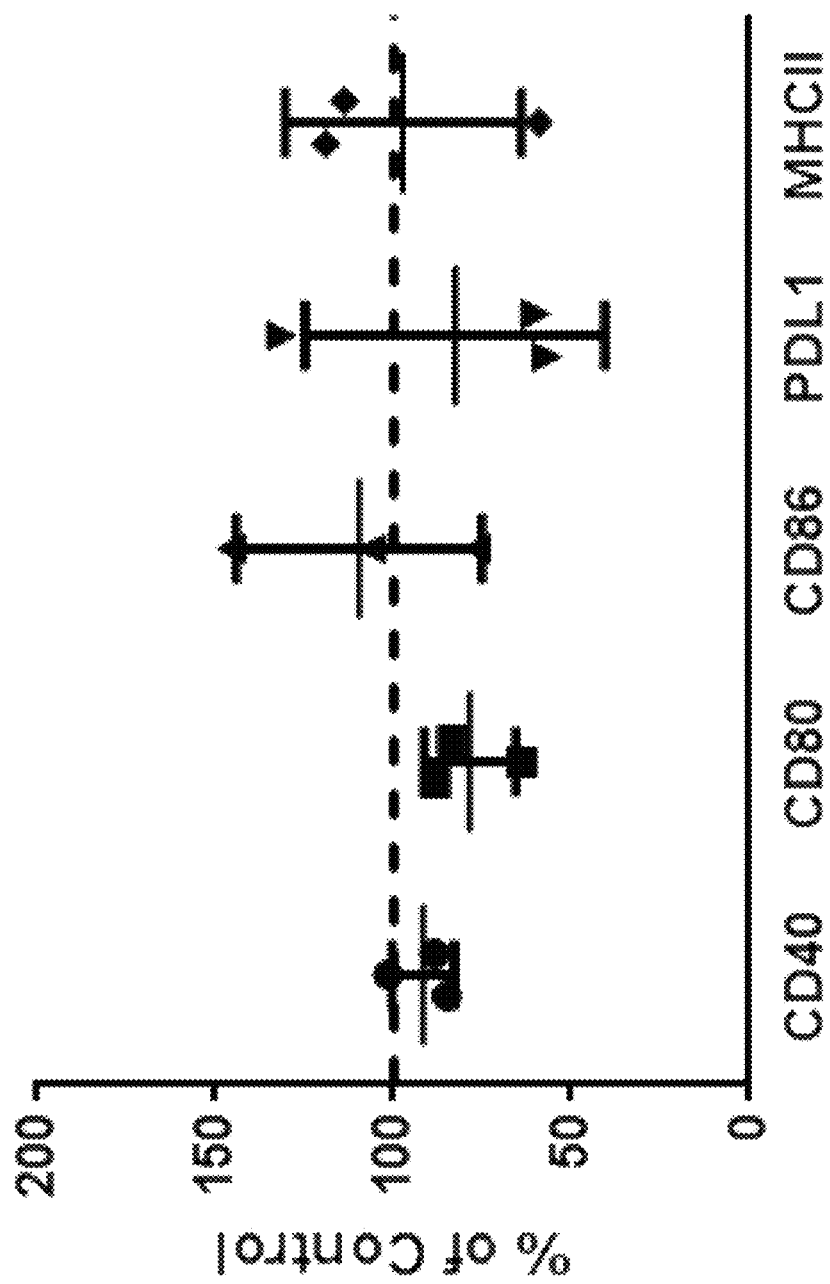

The pDC from livers of WT or miR-181a$^{-/-}$ (KO) C57BL/6J mice were examined by flow cytometry for the expression of classic costimulatory ligands CD40, CD80, and CD86; coinhibitory ligand programmed death ligand-1 (PD-L1); and MHCII. Geomeans measured on KO were expressed as a percentage compared to the WT geomean (FIG. 3A). Next, the effects of a TLR9 ligand were tested. Mice were injected intravenously (i.v.) 16 hours prior to isolation of liver pDC with 100 µg of the TLR9 ligand, CpG A ODN2216 and subjected to flow cytometric analysis (FIG. 3B). The results show that the classic costimulatory molecule CD86 and major histocompatibility complex (MHC) II are more highly expressed in hepatic pDC from miR-181a$^{-/-}$ mice than in WT mice when freshly isolated, but this difference is negated when cells are stimulated by TLR9.

Conclusions

Hepatic plasmacytoid DC prolonged cardiac allograft survival (p<0.01) in a murine model compared to bulk DC. The expression of miR-181a was significantly elevated in hepatic plasmacytoid DC compared to myeloid DC. In order to evaluate the role of miR-181a in inducing tolerance in plasmacytoid DC, we isolated plasmacytoid DC from miR-181a$^{-/-}$ mice and tested their effects in the same murine model of cardiac allograft transplantation. The plasmacytoid DC from miR-181a$^{-/-}$ mice abrogated the tolerogenic properties seen with hepatic plasmacytoid DC. CD86 and major histocompatibility complex II were more highly expressed in the freshly isolated miR-181a$^{-/-}$ liver plasmacytoid DC than in wild-type liver plasmacytoid DC. Together, this data shows that miR-181a plays a critical role in the tolerance-inducing properties of plasmacytoid DC.

Materials and Methods miRNA Isolation

Total miRNA was isolated using the mirVana miRNA isolation kit (all products from Applied Biosystems, Foster City, Calif.), as described previously (Wei et al. (2012) AJT 12(5):1113-1123; herein incorporated by reference). The miRNA of interest were further quantitated by real-time polymerase chain reaction (PCR).

Statistical Analyses

Statistical analyses were performed using the 2-tailed Student's t and Mann-Whitney tests with a p value of <0.05 considered to be significant. Graft survival data was compared by Kaplan-Meier analysis and the log-rank test. Results are expressed as means±1 SD.

Example 2

Adoptive Cell Transfer with Modified Dendritic Cells

We have shown that miR-181a confers tolerogenicity on pDC. By silencing or enhancing this miRNA in dendritic cells, we can modulate the immune responsiveness of dendritic cells, either conferring tolerogenic properties or enhancing immunity. We are designing siRNAs that target miR-181a to downregulate its expression as well as mimics of miR-181a and testing their effects in bone marrow derived pDC (BMpDC). The effects are analyzed by confirming that appropriate downstream targets are affected by PCR or western blot. Additionally, functional changes in modified BMpDC are assessed by analyzing cytokine production (ELISA or luciferase assays); surface phenotypic markers (FACS analysis); and T cell activation (MLR, FACS, ELISA).

The manner in which DC are activated can alter their potential to induce tolerance or immunity. HpDC from C57BL/10 or BMpDC can be modified by transfecting with either a microRNA inhibitor or mimic of miR-181a to enhance or suppress an immune response, respectively. For example, treatment of recipient mice using adoptive transfer of modified donor HpDC, transfected with a miR-181a mimic, administered to small intestinal allograft recipients, can prolong allograft survival by modifying the recipient immune response towards donor antigens. Wild-type BALB/c are transplanted with syngeneic (BALB/c) or allogeneic (C57BL/10) vascularized, orthotopic SI grafts as described previously (Krams et al. (2010) Transplantation 90:1272-1277; herein incorporated by reference in its entirety). Animals either receive no treatment or are injected i.v. with 1-1.5×10$^6$ Allo-Ag (BALB/c) pulsed HpDC [either syngeneic, allogeneic, or third party (C3H)] at day −7, 0, or +1 from Tx. One mouse from each group is sacrificed on days 2, 4, and 6, and intestinal tissue is obtained for histopathologic analyses as well as analysis by flow cytometry and RT-PCR for TLR and cytokine analysis. The remainder of mice are followed for survival to determine if adoptive transfer with HpDC and modified BMpDC results in prolonged Allo-Ag specific allograft survival.

In addition, short-term immunosuppressive drugs (e.g. Tacrolimus) and/or co-stimulatory blockade agents (e.g., CTLA4Ig or anti-CD154) can be combined with adoptive transfer of modified HpDC to help promote DC tolerogenicity. Animals that survive for at least 100 days are sacrificed and their $T_{reg}$ cells are examined for antigen-specificity and function.

Example 3

Microarray Analysis of MicroRNA Expression in Dendritic Cells

Quality total RNA (RIN>7) was extracted from FACS sorted murine dendritic cells (DC) as per the manufacturer's protocol (miRNeasy Qiagen) and assayed for expression using Affymetrix Genechip arrays. The miRNA from wild type C57BL/6J bulk, conventional and plasmacytoid DCs were quantified using the miRNA 4.0 array as per the manufacturer's recommendations by the Stanford PAN Facility.

Intensity data for the miRNA arrays were assessed for quality control after probe summarization and background correction, and log$_2$ transformed, normalized, then converted to expression values by liner modeling using robust multi-array averaging (RMA (Irizarry et al. (2003) Biostatistics 4(2):249-264; herein incorporated by reference)) in the Affymetrix Expression Console (Affymetrix, Santa Clara, Calif.). Differential expression was determined using significance analysis of microarrays (SAM (Tusher et al. (2001) Proc. Natl. Acad. Sci. U.S.A. 98(9):5116-5121; herein incorporated by reference) using a false discovery rate (FDR) adjusted Q-value of less than 10%. The top 30 differentially regulated miRNAs are shown in Table 1.

TABLE 1

Top 30 differentially regulated miRNAs in plasmacytoid dendritic cells compared to bulk and conventional dendritic cells

| miRNA symbol | Fold change | Q value (%) |
|---|---|---|
| mmu-miR-592-5p | 21.92 | 0.00 |
| mmu-miR-181a-1-3p | 5.88 | 0.00 |
| mmu-miR-181b-5p | 5.27 | 0.00 |
| mmu-miR-532-3p | 4.73 | 0.00 |
| mmu-miR-501-3p | 4.08 | 0.00 |
| mmu-miR-467a-5p | 3.74 | 0.00 |
| mmu-miR-532-5p | 3.40 | 0.00 |
| mmu-mir-181a-2 | 2.49 | 0.00 |
| mmu-miR-181a-5p | 2.47 | 0.00 |
| mmu-miR-669a-5p | 4.70 | 0.81 |
| mmu-miR-138-5p | −188.43 | 0.00 |
| mmu-miR-187-3p | −173.35 | 0.00 |
| mmu-miR-138-1-3p | −25.75 | 0.00 |
| mmu-miR-223-3p | −24.11 | 0.00 |
| mmu-miR-326-3p | −23.52 | 0.00 |
| mmu-miR-27a-5p | −22.65 | 0.00 |
| mmu-miR-3107-5p | −18.92 | 0.00 |
| mmu-miR-486-5p | −18.92 | 0.00 |
| mmu-miR-187-5p | −16.47 | 0.00 |
| mmu-miR-212-3p | −14.38 | 0.00 |
| mmu-miR-140-5p | −14.29 | 0.00 |
| mmu-miR-3473f | −14.07 | 0.00 |
| mmu-miR-23a-5p | −12.80 | 0.00 |
| mmu-miR-34a-5p | −12.37 | 0.00 |
| mmu-miR-182-5p | −8.84 | 0.00 |
| mmu-miR-3470b | −6.67 | 0.00 |
| mmu-miR-25-5p | −6.63 | 0.00 |
| mmu-miR-15a-3p | −6.34 | 0.00 |
| mmu-miR-30b-3p | −6.32 | 0.00 |
| mmu-miR-1946b | −6.15 | 0.00 |

While the preferred embodiments of the invention have been illustrated and described, it will be appreciated that various changes can be made therein without departing from the spirit and scope of the invention.

What is claimed is:

1. A host tolerogenic dendritic cell transfected with a miR-181 or a miR-181 mimic that makes the host dendritic cell tolerogenic.

2. The host tolerogenic dendritic cell of claim 1, wherein the miR-181 is selected from the group consisting of miR-181a, miR-181b, miR-181c, and miR-181d.

3. The host tolerogenic dendritic cell of claim 2, wherein the miR-181 comprises a sequence selected from the group consisting of SEQ ID NOS:1-6.

4. The host tolerogenic dendritic cell of claim 1, wherein the miR-181 or miR-181 mimic is provided by a recombinant polynucleotide comprising a promoter operably linked to a polynucleotide sequence encoding the miR-181 or the miR-181 mimic.

5. The host tolerogenic dendritic cell of claim 1, wherein the recombinant polynucleotide comprises a plasmid or a viral vector.

6. The host tolerogenic dendritic cell of claim 1, wherein the dendritic cell is a plasmacytoid dendritic cell or a myeloid dendritic cell.

7. The host tolerogenic dendritic cell of claim 1, wherein the host dendritic cell is human.

8. A composition comprising tolerogenic dendritic cells, said composition comprising the host tolerogenic dendritic cell of claim 1.

9. The composition of claim 8, wherein at least 95% of the dendritic cells in the composition are tolerogenic dendritic cells.

10. The composition of claim 8, further comprising a pharmaceutically acceptable excipient.

11. The composition of claim 8, further comprising an immunosuppressive drug or anti-inflammatory agent.

12. A method of increasing allograft tolerance in a subject, the method comprising administering a therapeutically effective amount of the composition of claim 8 to the subject.

13. The method of claim 12, wherein the subject has received an allogeneic tissue or organ transplant.

14. The method of claim 12, wherein the method is performed prior to performance of an allogeneic tissue or organ transplant.

15. The method of claim 12, wherein the method is performed in conjunction with an allogeneic tissue or organ transplant.

16. The method of claim 12, wherein the method is performed within at least two weeks after an allogeneic tissue or organ transplant.

17. The method of claim 12, wherein the composition is administered to prolong survival of a cardiac tissue transplant.

18. The method of claim 12, wherein the composition comprises plasmacytoid dendritic cells (pDC) or myeloid dendritic cells (mDC).

19. The method of claim 12, wherein the miR-181 or miR-181 mimic is provided by a recombinant polynucleotide comprising a promoter operably linked to a polynucleotide encoding the miR-181 or miR-181 mimic.

20. The method of claim 12, wherein the subject is human.

21. The method of claim 12, wherein at least 95% of the dendritic cells in the composition are tolerogenic dendritic cells.

22. The method of claim 12, wherein the composition is administered intravenously or intra-arterially.

23. The method of claim 12, wherein the composition is administered locally at the site of a tissue or organ transplant.

24. A kit comprising the composition of claim 8 and instructions for treating a condition or disease that would benefit from enhanced immune tolerance.

25. A method of producing the tolerogenic dendritic cell of claim 1, the method comprising:
   a) transfecting a host dendritic cell with a recombinant polynucleotide comprising a polynucleotide sequence encoding a miR-181 or a miR-181 mimic operably linked to a promoter; and
   b) culturing the host dendritic cell under conditions whereby the miR-181 or the miR-181 mimic is expressed to produce the tolerogenic dendritic cell of claim 1.

* * * * *